US012678511B2

(12) United States Patent
Kondo et al.

(10) Patent No.: US 12,678,511 B2
(45) Date of Patent: Jul. 14, 2026

(54) PEPTIDE AND USE THEREOF

(71) Applicant: Kansai Medical University Educational Corgoration, Hirakata (JP)

(72) Inventors: Eisaku Kondo, Niigata (JP); Ken Saito, Niigata (JP)

(73) Assignee: Kansai Medical University Educational Corporation, Osaka (JP)

( * ) Notice: Subject to any disclaimer, the term of this patent is extended or adjusted under 35 U.S.C. 154(b) by 1204 days.

(21) Appl. No.: 17/593,570

(22) PCT Filed: Feb. 27, 2020

(86) PCT No.: PCT/JP2020/007917
§ 371 (c)(1),
(2) Date: Sep. 21, 2021

(87) PCT Pub. No.: WO2020/195504
PCT Pub. Date: Oct. 1, 2020

(65) Prior Publication Data
US 2022/0175940 A1      Jun. 9, 2022

(30) Foreign Application Priority Data
Mar. 26, 2019    (JP) ................................. 2019-057966

(51) Int. Cl.
| | |
|---|---|
| *C07K 7/08* | (2006.01) |
| *A61K 47/36* | (2006.01) |
| *A61K 47/42* | (2017.01) |
| *A61K 47/64* | (2017.01) |
| *A61P 35/00* | (2006.01) |
| *C07K 7/06* | (2006.01) |

(52) U.S. Cl.
CPC .............. *A61K 47/64* (2017.08); *A61K 47/36* (2013.01); *A61K 47/42* (2013.01); *A61P 35/00* (2018.01); *C07K 7/06* (2013.01)

(58) Field of Classification Search
None
See application file for complete search history.

(56) References Cited

U.S. PATENT DOCUMENTS

| | | |
|---|---|---|
| 8,394,758 B2 | 3/2013 | Wu et al. |
| 2002/0102265 A1 | 8/2002 | Hong et al. |
| 2018/0360903 A1 | 12/2018 | Kondo et al. |
| 2019/0175684 A1 | 6/2019 | Fukuda et al. |

FOREIGN PATENT DOCUMENTS

| | | |
|---|---|---|
| CN | 107188948 A | 9/2017 |
| JP | 5721140 | 5/2015 |
| KR | 10-2015-0124910 A | 11/2015 |
| WO | 02/02147 A2 | 1/2002 |
| WO | 2011/130624 A2 | 10/2011 |
| WO | 2017086090 | 5/2017 |
| WO | 2017/176081 A1 | 10/2017 |
| WO | 2018034356 | 2/2018 |

OTHER PUBLICATIONS

NCBI entry (retrieved from https://www.ncbi.nlm.nih.gov/protein/XP_009010991.1?report=genbank&log$=protalign&blast_rank=16&RID=J72S6XU1016 on Oct. 31, 24, entry is dated Sep. 3, 2014, 2 pages) (Year: 2014).*
Blast search of SEQ ID No. 1 (retrieved from https://blast.ncbi.nlm.nih.gov/Blast.cgi on Mar. 10, 2025, 27 pages) (Year: 2025).*
BLAST search of SEQ ID No. 2 (retrieved from https://blast.ncbi.nlm.nih.gov/Blast.cgi on Aug. 19, 2025, 22 pages) (Year: 2025).*
NCBI entry for NUDIX hydrolase (retrieved from https://www.ncbi.nlm.nih.gov/protein/ACC73868.1?report=genbank&log$=protalign&blast_rank=1&RID=A9ABSUA7013 on Aug. 19, 2025; document dated Aug. 25, 2017, 2 pages) (Year: 2017).*
Supplementary European Search Report for EP20779187.2 mailed Jul. 11, 2022 (8 pages).
Gong Chun-ai et al. "Research progress of cell-penetrating peptides in tumor-targeted therapy" Second Millitary Medical University, vol. 38, the 6th , 2017, pp. from 774 to 779.
Tianjiao Ji, et al. "Peptide Assembly Integration of Fibroblast-Targeting and Cell-Penetration Features for Enhanced Antitumor Drug Delivery" Advanced Materials, vol. 27, the 11th, 2015, pp. form 1865 to 1873.

(Continued)

*Primary Examiner* — Ronald T Niebauer
(74) *Attorney, Agent, or Firm* — Knobbe, Martens, Olson & Bear, LLP

(57)      ABSTRACT

A peptide is composed of an amino acid sequence represented by general formula (I), and accumulates in cancer-associated fibroblasts. (In general formula (I), $X^{11}$ is a peptide residue composed of an amino acid sequence of (a) or (b) below: (a) an amino acid sequence represented by any one of SEQ ID NOs: 1 to 4, (b) an amino acid sequence in which one or two amino acids have been deleted, substituted or added in an amino acid sequence represented by any one of SEQ ID NOs: 1 to 4; $Y^{11}$ is a peptide linker composed of an amino acid residue of at least 1 but not more than 10 amino acids, wherein each amino acid residue is independently a glycine residue, a proline residue, a serine residue, a cysteine residue or a lysine residue; $X^{12}$ is either a peptide residue composed of an amino acid sequence of (a) or (b) above, or a retro-inverso peptide residue thereof; and n11 represents an integer of at least 0 but not more than 9.)

[Formula 1]

$$X^{11} - \left(Y^{11} - X^{12}\right)_{n11} \qquad (I)$$

14 Claims, 20 Drawing Sheets
Specification includes a Sequence Listing.

(56) References Cited

OTHER PUBLICATIONS

Chinese Office Action issued Nov. 10, 2023 in CN App. No. 202080022973.9.
Eric Vivès et al., "A Truncated HIV-1 Tat Protein Basic Domain Rapidly Translocates through the Plasma Membrane and Accumulates in the Cell Nucleus," The Journal of Biological Chemistry. 1997; 272(25): 16010-16017.
International Search Report of International Patent Application No. PCT/JP2020/007917 mailed on May 12, 2020.

* cited by examiner

Degradation test of peptides by 50% human plasma treatment using mass spectrometry analysis HE-stained image HE-stained image

PEPTIDE AND USE THEREOF

TECHNICAL FIELD

The present invention relates to a peptide and use of that peptide. Specifically, the present invention relates to a peptide having a high degree of accumulation in at least one of cancer-associated fibroblasts and mesenchymal stem cells contained in scirrhous carcinomas, a nucleic acid that encodes the peptide, a peptide-drug conjugate containing the peptide, a pharmaceutical composition containing the peptide-drug conjugate, a labeled peptide containing the peptide, an imaging composition containing the labeled peptide, and a peptide-drug conjugate expression vector and a labeled peptide expression vector each having the above nucleic acid. Priority is claimed on Japanese Patent Application No. 2019-057966, filed Mar. 26, 2019, the content of which is incorporated herein by reference.

BACKGROUND ART

In Japan, which has now reached the state of a super-aging society, malignant neoplasms currently represent the leading primary cause of death, with one in every two adults being affected. Among these malignant tumors, scirrhous carcinoma is one type of cancer that is resistant to current anticancer drug treatments, and is known as an intractable cancer for which improved treatments are essentially required. Depending on the histopathology of the tumor tissue, pancreatic cancer, stomach cancer, colon cancer and subtypes of breast cancer are recognized as representative examples of this type of poor prognosis scirrhous cancer.

Scirrhous carcinoma is well recognized by cancer clinicians as an intractable type of cancer that remains difficult to be curably treated and has one of the lowest survival rates. In Japan, each year about 18,000 people are diagnosed with pancreatic cancer and about 45,000 people are diagnosed with stomach cancer (10% of which are deemed scirrhous carcinoma), and these cancers have poor prognoses, with the number of deaths from pancreatic cancer exceeding 19,000 per year, and the five-year survival rate for scirrhous stomach cancer being between about 10% and 20%. According to an investigative report on nationwide pancreatic cancer registrations (1999), the number of cases of pancreatic cancer for which resection was possible represented approximately 39% of all cases, with the five-year survival rate for those resected cases being a very poor 13%. In other words, it can be stated that, even on a global level, scirrhous carcinoma is a highly aggressive tumor that requires urgent attention in the field of current medical treatment.

One of the reasons that scirrhous carcinoma is difficult to be curably treated is that pancreatic cancer and stomach cancer are hard to be found at early phase because of the lack of current clinical technologies to examine, and in most cases, by the time the cancer is diagnosed, the cancer is either beyond surgical indication, or has advanced and formed metastatic lesions. Another reason that makes curable treatment difficult is that scirrhous carcinoma has resistance to therapeutic medical treatments. This resistance is due to factors such as the well-developed fibrous cancer stroma acting as a physical barrier to the penetration of anticancer drugs and irradiation treatments. Further, this abundant cancer stroma establishes a biological interaction with the cancer cells that promotes proliferation, infiltration, and metastasis of the cancer cells, meaning the advance of the scirrhous carcinoma through the body is rapid, and the cancer is biologically highly aggressive. The main constituent components of this cancer stroma are known as cancer-associated fibroblasts (CAF), and it is known from existing research that one of the major source (cellular origin) for at least a portion of CAF is mesenchymal stem cells (MSC) incorporated within the cancer tissue. Furthermore, in pancreatic cancer and the like, the development of blood vessels in the abundant stroma portion that surrounds the periphery of the cancer cells is poor, reducing the expectation for the enhanced permeation and retention (EPR) effect that can be achieved for anticancer drugs in tumor tissue via blood vessels, and therefore the therapeutic effects of drug administration tend to be tenuous, with control of this thickly developed cancer stroma representing a considerable problem in all similar types of cancer.

Incidentally, among trends in the pharmaceutical field for the utilization of peptides as biomaterials, cell-penetrating (cell-absorbable) peptides such as Tat, Penetratin and poly-arginine are attracting much attention. However, these peptides are absorbed extensively and non-selectively, with no distinction between normal cells or normal tissue and tumor cells or tumor tissue. Accordingly, application of these peptides to medical treatment DDS (drug delivery system) tools for patient malignant tumors including solid carcinomas, which requires target-selective drug delivery, is problematic due to the severe side-effects. In particular, cell-penetrating (cell-absorbable) peptides such as Tat that have been widely used in experimental systems around the world are known to cause accumulation in the liver (for example, see non-Patent Document 1).

In contrast, cyclic RGD is the only medicated peptide. Cyclic RGD targets the $\alpha_v\beta_3$ integrin that has been reported to be expressed highly in new blood vessels or vascular endothelial cells that constitute existing blood vessels (and in some tumor cells), acts through vascular hyperpermeability, and is expected to offer a drug transport effect by enhancement of the EPR effect (a substance diffusion effect via blood vessels). Accordingly, cyclic RGD is not used alone, but is rather used simultaneously in combination with another drug as an imaging agent or DDS agent (for example, see Patent Document 1). However, the permeability and action of cyclic RGD relative to cancer cells themselves is extremely poor, with the cyclic RGD system offering mainly a drug diffusion effect via the blood vessels that is largely dependent on the structure (development and distribution of blood vessels) of the tumor tissue. For these reasons, a satisfactory effect cannot be expected in those cases where an anticancer treatment based on direct elimination of the cancer cells themselves is being targeted.

In order to address the types of issues outlined above, the inventors of the present invention have been developing peptides which act directly on pancreatic cancer cells or pancreatic cancer tissue, and act directly on (are incorporated into) tumors via highly shifted absorption (for example, see Patent Document 2).

However, a short-chain peptide capable of minimizing absorption into normal cells and normal tissue while exhibiting highly shifted absorption into scirrhous carcinoma tissue containing large amounts of CAF has yet to be developed.

PRIOR ART LITERATURE

Patent Documents

Patent Document 1: Japanese Patent (Granted) Publication No. 5721140

3

Patent Document 2: International Patent Publication No. 2017/086090

Non-Patent Document

Non-Patent Document 1: Vives E., et al., A Truncated HIV-1 Tat Protein Basic Domain Rapidly Translocates through the Plasma Membrane and Accumulates in the Cell Nucleus, J. Biol. Chem., 272, 16010-16017, 1997.

DISCLOSURE OF INVENTION

Problems to be Solved by the Invention

The present invention has been developed in light of the above circumstances, and provides a novel peptide that accumulates selectively in CAF, as well as providing a nucleic acid that encodes the peptide, a peptide-drug conjugate containing the peptide, a pharmaceutical composition containing the peptide-drug conjugate, a labeled peptide containing the peptide, an imaging composition containing the labeled peptide, and a peptide-drug conjugate expression vector and a labeled peptide expression vector each containing the above nucleic acid.

Means for Solving the Problems

As a result of intensive research aimed at achieving the objects described above, the inventors of the present invention identified a peptide having highly shifted absorption in mesenchymal stem cells which migrate into cancer tissue and differentiate into CAF within the tumor, and discovered that this peptide exhibited suppressed absorption into normal cells and normal tissue, while exhibiting a high-degree of selective accumulation in CAF differentiated from MSC within the tumor tissue, and they were thus able to complete the present invention.

In other words, the present invention includes the following aspects.

A peptide according to a first aspect of the present invention is composed of an amino acid sequence represented by general formula (I) shown below.

[Formula 1]

$$X^{11} - \left(Y^{11} - X^{12}\right)_{n11} \qquad \text{(I)}$$

(In general formula (I), $X^{11}$ is a peptide residue composed of an amino acid sequence of (a) or (b) below:

(a) an amino acid sequence represented by any one of SEQ ID NOs: 1 to 4, (b) an amino acid sequence in which one or two amino acids have been deleted, substituted, or added in an amino acid sequence represented by any one of SEQ ID NOs: 1 to 4;

$Y^{11}$ is a peptide linker composed of an amino acid residue of at least 1 but not more than 10 amino acids, wherein each amino acid residue is independently a glycine residue, a proline residue, a serine residue, a cysteine residue, or a lysine residue;

$X^{12}$ is either a peptide residue composed of an amino acid sequence of (a) or (b) above, or a retro-inverso peptide residue thereof; and n11 represents an integer of at least 0 but not more than 9.)

$Y^{11}$ may be a peptide linker composed of a glycine residue of at least 1 but not more than 10 amino acids.

Further, n11 may be an integer of at least 1 but not more than 4.

$X^{11}$ and $X^{12}$ may be peptide residues composed of the same amino acid sequence.

The peptide according to the first aspect described above may be composed of an amino acid sequence represented by SEQ ID NO: 5.

A nucleic acid according to a second aspect of the present invention encodes the peptide according to the first aspect described above.

A peptide-drug-conjugate according to a third aspect of the present invention comprises the peptide according to the first aspect described above and a biologically active substance.

A pharmaceutical composition according to a fourth aspect of the present invention comprises the peptide-drug-conjugate according to the third aspect described above.

The pharmaceutical composition according to the fourth aspect may be used for treatment of scirrhous carcinomas.

The above biologically active substance may be an anti-cancer drug.

A labeled peptide according to a fifth aspect of the present invention comprises the peptide according to the first aspect described above and a labeling substance.

The labeling substance may be biotin, avidin, streptavidin, a stable isotope, a radioisotope, or a fluorescent substance.

An imaging composition according to a sixth aspect of the present invention comprises the labeled peptide according to the fifth aspect described above.

The imaging composition according to the sixth aspect may be used for scirrhous carcinomas.

The imaging composition according to the sixth aspect may be used for scirrhous carcinomas diagnosis.

A peptide-drug-conjugate expression vector according to a seventh aspect of the present invention has the nucleic acid according to the second aspect described above and a nucleic acid that encodes a biologically active substance.

A labeled peptide expression vector according to an eighth aspect of the present invention has the nucleic acid according to the second aspect described above and a nucleic acid that encodes a labeling substance.

Further, other aspects of the present invention are as follows.

(1) A peptide composed of an amino acid sequence represented by general formula (I) shown below.

[Formula 2]

$$X^{11} - \left(Y^{11} - X^{12}\right)_{n11} \qquad \text{(I)}$$

(In general formula (I), $X^{11}$ is a peptide residue composed of an amino acid sequence of (a) or (b) below:

(a) an amino acid sequence represented by any one of SEQ ID NOs: 1 to 4, (b) an amino acid sequence in which one or two amino acids have been deleted, substituted, or added in an amino acid sequence represented by any one of SEQ ID NOs: 1 to 4;

$Y^{11}$ is a peptide linker composed of an amino acid residue of at least 1 but not more than 10 amino acids, wherein each amino acid residue is independently a glycine residue, a proline residue, a serine residue, a cysteine residue, or a lysine residue;

$X^{12}$ is either a peptide residue composed of an amino acid sequence of (a) or (b) above, or a retro-inverso peptide residue thereof; and n11 represents an integer of at least 0 but not more than 9.)

(2) The peptide according to (1), wherein $Y^{11}$ is a peptide linker composed of a glycine residue of at least 1 but not more than 10 amino acids.

(3) The peptide according to (1) or (2), wherein n11 is an integer of at least 1 but not more than 4.

(4) The peptide according to any one of (1) to (3), wherein $X^{11}$ and $X^{12}$ are peptide residues composed of the same amino acid sequence.

(5) The peptide according to any one of (1) to (4), composed of an amino acid sequence represented by SEQ ID NO: 5.

(6) A nucleic acid that encodes the peptide according to any one of (1) to (5).

(7) A peptide-drug-conjugate comprising the peptide according to any one of (1) to (5) and a biologically active substance.

(8) A pharmaceutical composition comprising the peptide-drug-conjugate according to (7).

(9) The pharmaceutical composition according to (8), which is used for treatment of scirrhous carcinomas.

(10) The pharmaceutical composition according to (8) or (9), wherein the biologically active substance is an anticancer drug.

(11) A labeled peptide comprising the peptide according to any one of (1) to (5) and a labeling substance.

(12) The labeled peptide according to (11), wherein the labeling substance may be biotin, avidin, streptavidin, a stable isotope, a radioisotope, or a fluorescent substance.

(13) An imaging composition comprising the labeled peptide according to (11) or (12).

(14) The imaging composition according to (13), which is used for scirrhous carcinomas.

(15) The imaging composition according to (13) or (14), which is used for scirrhous carcinomas diagnosis.

(16) A peptide-drug-conjugate expression vector having the nucleic acid according to (6) and a nucleic acid that encodes a biologically active substance.

(17) A labeled peptide expression vector having the nucleic acid according to (6) and a nucleic acid that encodes a labeling substance.

Effects of the Invention

The peptide of the aspect described above provides a novel peptide that accumulates selectively in CAF.

EMBODIMENTS FOR CARRYING OUT THE INVENTION

<<Peptide Having Accumulation in CAF>>

Figure 1:
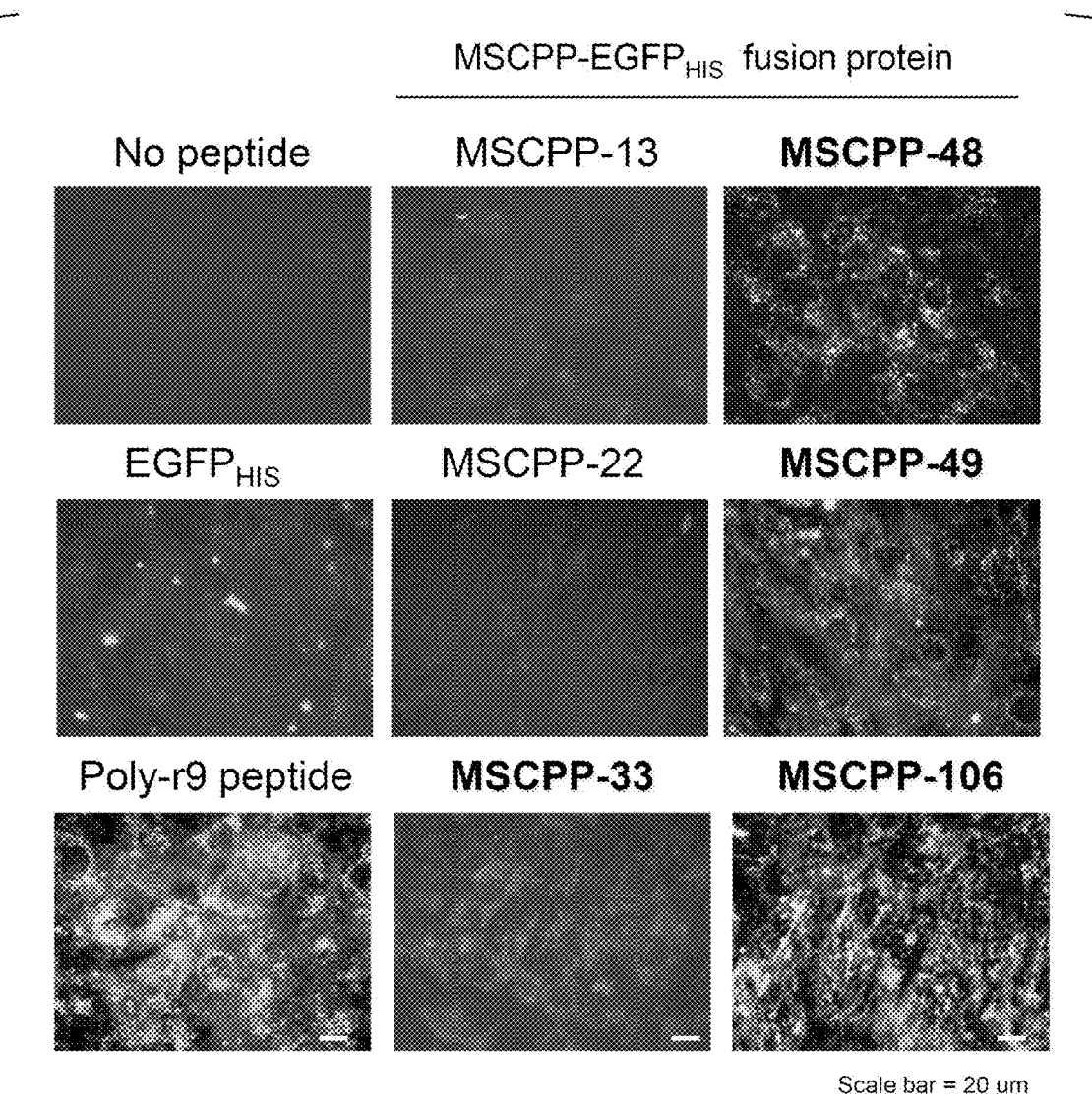
FIG. 1 is a series of fluorescent images of human mesenchymal stem cells (hMSC) to which various peptides have been added in Example 1. The scale bars indicate 20 μm.

A peptide of this embodiment is composed of an amino acid sequence represented by general formula (I) shown below.

[Formula 3]

$$X^{11} - \left( Y^{11} - X^{12} \right)_{n11} \tag{I}$$

(In general formula (I), $X^{11}$ is a peptide residue composed of an amino acid sequence of (a) or (b) below (hereafter sometimes referred to as "the amino acid sequence (I)"):

(a) an amino acid sequence represented by any one of SEQ ID NOs: 1 to 4, (b) an amino acid sequence in which one or two amino acids have been deleted, substituted, or added in an amino acid sequence represented by any one of SEQ ID NOs: 1 to 4;

$Y^{11}$ is a peptide linker composed of an amino acid residue of at least 1 but not more than 10 amino acids, wherein each amino acid residue is independently a glycine residue, a proline residue, a serine residue, a cysteine residue, or a lysine residue;

$X^{12}$ is either a peptide residue composed of an amino acid sequence of (a) or (b) above, or a retro-inverso peptide residue thereof; and n11 represents an integer of at least 0 but not more than 9.)

Pancreatic cancer tissue, which represents one example of scirrhous carcinoma, is composed of an invasive cell nest formed from the cancer cells and a thick well-developed stroma, and if this stroma is destroyed, the tumor disintegrates. For this reason, medical treatments targeting the cancer stroma are currently being investigated. The inventors of the present invention focused their attention on the cancer-associated fibroblasts (CAF) contained within the cancer stroma, and, as illustrated in the examples below, identified a peptide having good accumulation in mesenchymal stem cells (MSC) which are known to differentiate into CAF within cancer tissue, and discovered that this peptide exhibited suppressed absorption into normal cells and normal tissue, while exhibiting selective accumulation in the CAF in scirrhous carcinoma tissue, enabling them to complete the present invention.

In this description, a "scirrhous carcinoma" describes a type of cancer having a tissue morphology with abundant stroma cells formed mainly from the fibroblasts seen in malignant tumors, wherein the cancer cells infiltrate diffusely with this abundant stroma in the background. A scirrhous carcinoma is also termed a "hard cancer".

Specific example of scirrhous carcinoma include invasive pancreatic ductal adenocarcinoma, poorly differentiated stomach adenocarcinoma, invasive breast ductal carcinoma, and diffuse invasive colon carcinoma.

Scirrhous carcinoma is an example of a type of cancer for which CAF development is marked, but CAF are incorporated in the tissue of all tumors that develop in the human body, irrespective of the amount. Accordingly, although the principal objective of the peptide of this embodiment involves application to scirrhous carcinoma, the peptide is actually widely applicable to all types of cancer.

In this description, a "high degree of accumulation in CAF" describes a property wherein the peptide is absorbed and accumulated to a higher degree in CAF or cancer stroma, compared with the degree of accumulation in normal tissue in the body and malignant tumor cells of other strains. Further, as illustrated in the examples described below, the peptide of the present embodiment is also absorbed and accumulated to a high degree in MSC which function as the cellular origin for CAF. Accordingly, the peptide of the present embodiment can be described as a peptide that is absorbed and accumulates to a high degree in CAF, MSC, and cancer stroma containing CAF and/or MSC.

<Amino Acid Sequence (I)>

The amino acid sequence (I) is a sequence represented by general formula (I) shown below.

[Formula 4]

$$X^{11} - \left(Y^{11} - X^{12}\right)_{n11} \qquad (I)$$

$[X^{11}]$

In general formula (I), $X^{11}$ is a peptide residue composed of an amino acid sequence of (a) or (b) below:

(a) an amino acid sequence represented by any one of SEQ ID NOs: 1 to 4, (b) an amino acid sequence in which one or two amino acids have been deleted, substituted, or added in an amino acid sequence represented by any one of SEQ ID NOs: 1 to 4.

The amino acid sequences represented by SEQ ID NO: 1, 2, 3 or 4 in (a) above are the amino acid sequences shown below.

|  |  |
|---|---|
| KCAELFRHL | (SEQ ID NO: 1) |
| WPPLQRWRN | (SEQ ID NO: 2) |
| RTHPVWSRT | (SEQ ID NO: 3) |
| RRWMQWPWH | (SEQ ID NO: 4) |

In general formula (I), $X^{11}$ may be a peptide residue composed of an amino acid sequence of (b) described below, which represents a peptide residue that is functionally equivalent to the peptide residue composed of an amino acid sequence of (a) described above.

(b) An amino acid sequence in which one or two amino acids have been deleted, substituted, or added in an amino acid sequence represented by any one of SEQ ID NOs: 1 to 4.

In this description, the term "substituted" means substitution with another amino acid residue having a chemically similar side chain. Groups of amino acid residues having chemically similar amino acid side chains are well known in the technical field to which polypeptides obtained using the production method of an embodiment of the present invention belong. For example, among acidic amino acids (aspartic acid and glutamic acid), basic amino acids (lysine, arginine and histidine) and neutral amino acids, classification can be made into amino acids having a hydrocarbon chain (glycine, alanine, valine, leucine, isoleucine and proline), amino acids having a hydroxyl group (serine and threonine), amino acids containing sulfur (cysteine and methionine), amino acids having an amide group (asparagine and glutamine), amino acids having an imino group (proline), and amino acids having an aromatic group (phenylalanine, tyrosine and tryptophan) and the like. The most commonly occurring amino acid substitutions include, for example, alanine/serine, valine/isoleucine, aspartic acid/glutamic acid, threonine/serine, alanine/glycine, alanine/threonine, serine/asparagine, alanine/valine, serine/glycine, tyrosine/phenylalanine, alanine/proline, lysine/arginine, aspartic acid/asparagine, leucine/isoleucine, leucine/valine, alanine/glutamic acid, and aspartic acid/glycine.

More specifically, in the amino acid sequence represented by SEQ ID NO: 1, possible substitutions that can be envisaged include substitution of the lysine first from the N-terminus with glycine, alanine, arginine, histidine, serine or threonine, and substitution of the leucine first from the C-terminus with glycine, alanine, isoleucine, proline or valine.

Further, the peptide residue composed of an amino acid sequence of (a) or (b) above may be composed of L-amino acids, D-amino acids, or a combination thereof. Among the various possibilities, $X^{11}$ is preferably a peptide residue composed of L-amino acids.

L-amino acids are amino acids that exist in nature, whereas a D-amino acid is an amino acid in which the chirality of an L-amino acid residue has been reversed. Further, in order to enhance the high degree of accumulation in cancer stroma containing CAF or MSC, or in order to optimize other physical properties, the amino acid residues that constitute the peptide residue composed of an amino acid sequence of (a) or (b) above may be subjected to chemical modification such as methylation or addition of a sugar chain.

[$X^{12}$]

In general formula (I), $X^{12}$ is either a peptide residue composed of an amino acid sequence of (a) or (b) above, or a retro-inverso peptide residue thereof.

In this description, a "retro-inverso peptide residue" means a peptide residue in which the amino acid sequence is reversed, and substituted with enantiomeric amino acid residues.

Among the various possibilities, from the viewpoint of further enhancing the high degree of accumulation in cancer stroma containing CAF or MSC, $X^{12}$ is preferably a peptide residue having the same amino acid sequence as $X^{11}$. Further, from the viewpoint of achieving superior degradation resistance in vivo, $X^{12}$ is preferably a retro-inverso peptide residue of $X^{11}$.

[$Y^{11}$]

In general formula (I), $Y^{11}$ is a peptide linker composed of an amino acid residue of at least 1 but not more than 10 amino acids. The number of amino acids in $Y^{11}$ is preferably at least 1 but not more than 5, more preferably at least 1 but not more than 3, and even more preferably 1.

Among the various possibilities, $Y^{11}$ is preferably a peptide linker composed of an amino acid residue of at least 1 but not more than 10 amino acids, wherein each amino acid residue is independently a glycine residue, a cysteine residue, or a lysine residue, and is more preferably a peptide linker composed of an amino acid residue having one amino acid, wherein the amino acid residue is a glycine residue, a cysteine residue, or a lysine residue. In those cases where the amino acid residue that constitutes $Y^{11}$ is a cysteine residue or a lysine residue, a target substance described below can be bonded covalently to the peptide of the present embodiment via the thiol group (—SH) of the cysteine residue or the side chain of the lysine residue.

[n11]

In general formula (I), n11 represents an integer of at least 0 but not more than 9, and is preferably an integer of at least 0 but not more than 8, more preferably an integer of at least 0 but not more than 6, even more preferably an integer of at least 1 but not more than 4, particularly preferably an integer of at least 1 but not more than 3, and most preferably an integer of at least 1 but not more than 2.

When n11 is 2 or greater, the pluralities of $Y^{11}$ and $X^{12}$ may each be the same or different, but are preferably the same in terms of ease of synthesis.

In the peptide of the present embodiment, specific examples of preferred forms of the amino acid sequence (I) include the amino acid sequences represented by SEQ ID NOs: 1 to 4 shown above, and amino acid sequences represented by SEQ ID NOs: 5 and 6 shown below. It should be noted that these amino acid sequences are merely examples of preferred forms of the amino acid sequence (I), and preferred forms of the amino acid sequence (I) are not limited to these particular sequences. In the amino acid sequence represented by SEQ ID NO: 6, the "mC" second and twelfth from the N-terminus indicate methylated cysteine residues.

(SEQ ID NO: 5)

KCAELFRHL-G-KCAELFRHL (SEQ ID NO: 6)

KmCAELFRHL-G-KmCAELFRHL

Among the various possibilities, as indicated in the examples described below, because the cysteine residues second and twelfth from the N-terminus are important for accumulation in CAF, a peptide composed of the amino acid sequence represented by SEQ ID NO: 5 is preferred as the peptide of the present embodiment.

<Method for Producing Peptide>

The peptide of an embodiment of the present invention may be produced using chemical synthesis methods, or may be produced using biological methods. Examples of the chemical methods include peptide solid-phase synthesis methods (such as the Boc solid-phase synthesis method and Fmoc solid-phase synthesis method). Examples of biological methods include methods using cell-free peptide synthesis systems or living cell peptide synthesis systems that employ an expression vector having a nucleic acid that encodes the peptide. Details regarding cell-free peptide synthesis systems and living cell peptide synthesis systems are described below.

<Nucleic Acid>

A nucleic acid of an embodiment of the present invention is a nucleic acid that encodes the peptide according to the embodiment described above.

By using the nucleic acid according to this embodiment, a peptide having a high degree of accumulation in cancer stroma containing CAF or MSC can be obtained.

Examples of the nucleic acid that encodes the peptide described above include nucleic acids composed of a base sequence represented by any of SEQ ID NOs: 7 to 11, or nucleic acids having any base sequence that is at least 80% identical, for example at least 85% identical, at least 90% identical or at least 95% identical, with a base sequence represented by any of SEQ ID NOs: 7 to 11, and has a combination that encodes each of the amino acids that function as constituent components of a peptide having a high degree of accumulation in cancer stroma containing CAF or MSC. The base sequence represented by SEQ ID NO: 7 is the base sequence of a nucleic acid that encodes a peptide composed of an amino acid sequence represented by the above SEQ ID NO: 1. The base sequence represented by SEQ ID NO: 8 is the base sequence of a nucleic acid that encodes a peptide composed of an amino acid sequence represented by the above SEQ ID NO: 2. The base sequence represented by SEQ ID NO: 9 is the base sequence of a nucleic acid that encodes a peptide composed of an amino acid sequence represented by the above SEQ ID NO: 3. The base sequence represented by SEQ ID NO: 10 is the base sequence of a nucleic acid that encodes a peptide composed of an amino acid sequence represented by the above SEQ ID NO: 4. The base sequence represented by SEQ ID NO: 11 is the base sequence of a nucleic acid that encodes a peptide composed of an amino acid sequence represented by the above SEQ ID NO: 5.

The sequence identity of the target base sequence relative to the reference base sequence can be determined, for example, in the following manner. First, the reference base sequence and the target base sequence are aligned. Here, each base sequence may include gaps so as to maximize the sequence identity. Subsequently, the number of matching bases in the reference base sequence and the target base sequence is calculated, and the sequence identity can then be determined using the formula shown below.

$$\text{Sequence identity} (\%) = [\text{number of matching bases}]/[$$

$$\text{total number of bases in target base sequence}] \times 100$$

The nucleic acid of the present embodiment may be incorporated within a vector.

The vector is preferably a protein expression vector. There are no particular limitations on the expression vector, and examples of expression vectors that may be used include plasmids derived from *E. coli*, plasmids derived from *Bacillus subtilis*, plasmids derived from yeast, bacteriophages, virus vectors, and modified vectors thereof. Examples of the plasmids derived from *E. coli* include pBR322, pBR325, pUC12 and pUC13. Examples of the plasmids derived from *Bacillus subtilis* include pUB110, pTP5, and pC194. Examples of the plasmids derived from yeast include pSH19 and pSH15. Examples of the bacteriophages include A phage. Examples of viruses that yield virus vectors include adenovirus, adeno-associated virus, lentivirus, vaccinia virus, baculovirus, retrovirus and hepatitis virus.

In the above expression vector, there are no particular limitations on the promoter for the peptide expression, which may be an expression promoter that uses animal cells as a host, an expression promoter that uses plant cells as a host, or an expression promoter that uses insect cells as a host. Examples of expression promoters that use animal cells as a host include an EF1α promoter, SRα promoter, SV40 promoter, LTR promoter, CMV (cytomegalovirus) promoter, HSV-tk promoter and CAG promoter. Examples of expression promoters that use plant cells as a host include a cauliflower mosaic virus (CaMV) 35S promoter and an REF (rubber elongation factor) promoter. Examples of expression promoters that use insect cells as a host include a polyhedrin promoter and p10 promoter. These promoters may be selected appropriately in accordance with the type of host used for expressing the peptide.

The expression vector described above may further have a multicloning site, an enhancer, a splicing signal, a poly A addition signal, a selection marker, or a replication origin or the like.

The expression vector preferably has an added nucleic acid or separate target gene that encodes a stuffer protein such as green fluorescent protein (GFP) or glutathione-S-transferase (GST) (wherein the protein itself has low toxicity and exhibits no inherent function) either upstream or downstream from the nucleic acid that encodes the above peptide. This enables more efficient production of a fusion protein in which the above peptide is fused to the stuffer protein. Further, in the case of incorporation within an expression vector having an extracellular protein secretion signal, a fusion protein having the added amino acid sequence of the peptide can be produced in the culture solution and collected. Furthermore, even in the case of an intracellular expression vector, the same peptide-added fusion protein can still be produced.

By using an expression vector having a nucleic acid according to the present embodiment and suitable host cells, the peptide described above can be expressed.

<Modulator>

The peptide of an embodiment of the present invention may be modified with a modulator separately from the target substance described below. Examples of the modulator include sugar chains and polyethylene glycol (PEG). Further, liposomes, viruses, dendrimers, antibodies (immunoglobuins), exosomes, and polymer micelles and the like may also be used as modulators. In other words, the peptide of an embodiment of the present invention can be used in a form bonded to the expression of a liposome, virus, exosome or polymer micelle, a form in which either one, or a plurality of two or more of the peptides are bonded to the side-chain portion of a dendrimer, or a form in which an antibody (immunoglobulin) and the peptide are bonded together.

Examples of the dendrimer include poly(amidoamine) (PAMAM) dendrimers, polypropyleneimine dendrimers, polylysine dendrimers, polyphenyl ether dendrimers, and polyphenylene dendrimers. By using these dendrimers, from several tens of molecules through to one hundred and several tens of molecules of the peptide can be delivered simultaneously into the CAF or cancer stroma.

Further, by modifying the peptide of an embodiment of the present invention with a modulator described above, a target substance (for example, a biologically active substance or labeling substance) can be absorbed more easily and more efficiently into the CAF or cancer stroma. The peptide that has been modified with the modulator (hereafter sometimes abbreviated as a "modified peptide") can be prepared, for example, by physically or chemically bonding the modulator and the peptide, either directly or via a linker. Specific examples of the bonding method include coordination bonding, covalent bonding, hydrogen bonding, hydrophobic interactions and physical adsorption, and any conventional bonding, linkers or bonding methods may be employed. Further, the modulator bonding position may be either the N-terminus or the C-terminus of the peptide. Furthermore, in those cases where the peptide contains a lysine residue, the modulator may also be bonded to a side-chain site on the lysine residue.

<Target Substance>

The target substance may be selected appropriately in accordance with the intended application, and for example, in the case of use for imaging CAF or cancer stroma, a labeling substance may be used as the target substance, in the manner described below. Further, for example, in the case of use in an application for the treatment of scirrhous carcinoma, a biologically active substance (and in particular an anticancer drug) may be used as the target substance, in the manner described below. The peptide of an embodiment of the present invention can be used to deliver a single type of one of these target substances, or may be used to deliver a combination of two or more types of target substances.

The target substance may be bonded physically or chemically to the peptide, either directly or via a linker. Specific examples of the bonding method include coordination bonding, covalent bonding, hydrogen bonding, hydrophobic interactions and physical adsorption, and any conventional bonding, linkers or bonding methods may be employed. Further, the bonding position between the target substance and the peptide of an embodiment of the present invention may be selected appropriately according to need. Moreover, even in those cases where there is no physical or chemical bonding, a state in which the steric structure causes one of the molecules to restrict movement of the other molecule so that the two move together is included within the definition of a bonded state in this embodiment.

In those cases where the target substance is a protein, a fusion protein containing the target substance and the peptide can be produced, for example, in the following manner. First, an expression vector containing a nucleic acid that encodes the fusion protein is used to transform a host. Subsequently, the host is cultured to express the fusion protein. Conditions such as the composition of the culture medium, the culture temperature, the time, and the addition of an inducer and the like may be determined by those skilled in the art based on conventional methods so that the transformant grows and the fusion protein is produced efficiently. For example, when an antibiotic-resistant gene is incorporated into the expression vector as a selection marker, the transformant can be selected by adding an antibiotic to the medium. Subsequently, by purifying the fusion protein expressed by the host using an appropriate method, the fusion protein can be obtained.

There are no particular limitations on the host, provided it is composed of living cells capable of expressing an expression vector containing a nucleic acid that encodes the fusion protein. Examples of the host include mammalian cell lines such as Chinese hamster ovary (CHO) cells, viruses (for example, viruses such as adenovirus, adeno-associated virus, lentivirus, vaccinia virus, baculovirus, retrovirus and hepatitis virus), microorganisms such as bacteria (for example, *E. coli*), and living cells such as yeast cells, insect cells and plant cells.

Next, a peptide-drug conjugate (PDC), a pharmaceutical composition, a labeled peptide, and an imaging composition, each containing the peptide of an embodiment of the present invention, are described below in detail.

<<Peptide-Drug Conjugate (PDC)>>

A PDC of an embodiment of the present invention contains the peptide described above and a biologically active substance.

The PDC of this embodiment can selectively treat cancer (and particularly scirrhous carcinoma).

In this description, there are no particular limitations on the "biologically active substance", provided it is effective in treating human cancer, and examples include drugs such as anticancer drugs, nucleic acids, proteins having a cell growth inhibiting effect or a cytotoxic effect, antibodies or antibody fragments thereof that bind specifically to cancer cells, and aptamers.

For example, an antibody or antibody fragment thereof mentioned above may be bonded to the N-terminus or C-terminus of the peptide described above via a mediator such as a linker or via an amino acid sequence used as a spacer, or the peptide described above may be bonded to any site or a plurality of sites in the Fc domain of the antibody or antibody fragment thereof, thus forming an antibody-peptide conjugate. Because this antibody-peptide conjugate can bind not only to cell membrane surface antigens recognized by the antibody, but can simultaneously bind to cell membrane surface receptors recognized by the peptide, the delivery function to the targeted cells (CAF in the present embodiment) can be enhanced. Furthermore, in those cases where the antibody or antibody fragment thereof is a single-chain antibody (ScFv) capable of reacting with an intracellular antigen, by preparing an expression vector having a sequence that encodes the above peptide added to a nucleic acid that encodes the ScFv, a single-chain antibody having a delivery function to the target cells (CAF in the present embodiment) can be produced.

The "biologically active substance" is preferably a cytotoxic drug or molecular targeted drug that functions as an anticancer drug. Because the peptide described above exhibits absorption shifted to a high degree toward CAF or cancer stroma compared with normal cells and normal tissue, when the peptide is conjugated to form a PDC with a cytotoxic drug used as a conventional anticancer drug as the biologically active substance, that cytotoxic drug can be delivered efficiently to the cancer cells or cancer stroma that constitutes a scirrhous carcinoma.

The PDC of the present embodiment may also contains a peptide having a high degree of accumulation in cancer cells or cancer tissue of scirrhous carcinoma. By including a peptide having a high degree of accumulation in cancer cells or cancer tissue of scirrhous carcinoma, when the PDC is administered, for example, together with a biologically active substance having an anticancer effect, both the cancer cells and cancer stroma that constitute a scirrhous carcinoma can be destroyed, and a synergistic treatment effect is obtained. Examples of the peptide having a high degree of accumulation in cancer cells or cancer tissue of scirrhous carcinoma include the peptide having a high degree of accumulation in pancreatic cancer cells or pancreatic cancer tissue disclosed in Patent Document 2. The peptide having a high degree of accumulation in cancer cells or cancer tissue of scirrhous carcinoma may be modified with an aforementioned modulator.

The biologically active substance and the peptide are preferably bonded together to form a conjugate. Here, the term "conjugate" describes a state where two or more substances are able to move together, and includes cases where the substances are boned together by covalent boding, cases where the substances are electrostatically bonded by ionic bonding, and cases in which even if no bonding exists, the steric structure causes one of the substances to restrict movement of another substance so that the substances can move together. For example, cases in which the biologically active substance is enclosed within a liposome, virus, exosome, or polymer micelle or the like that has been surface-modified with the peptide are also included in cases of "conjugate" formation. Among the various possibilities, in order to inhibit dissociation of the biologically active substance prior to reaching the target site, the bonding between the biologically active substance and the peptide is preferably composed of covalent bonding.

Further, the above peptide having a high degree of accumulation in cancer cells or cancer tissue of scirrhous carcinoma may also be used to form a conjugate with a biologically active substance, or with the peptide described above and a biologically active substance.

Specific examples of methods for forming covalent bonding between the biologically active substance and the above peptide include methods that employ coupling reactions, either directly or via a linker, of the biologically active substance with an arbitrary site on the peptide having a functional group or with an introduced functional group such as —OH, —SH, —CO$_2$H, —NH$_2$, —SO$_3$H or —PO$_2$H. In a more specific example, an SH group (thiol group) is introduced into the peptide and a maleimide group is introduced into the biologically active substance, and the SH group of the peptide and the maleimide group of the biologically active substance are then bonded together, thereby bonding the peptide and the biologically active substance.

There are no particular limitations on the linker, provided it enables the functions of the biologically active substance and the peptide to be maintained, and is capable of passing through the cell membrane with the peptide. Specific examples of the linker include peptide chains having a length that is typically at least 1 residue but not more than 5 residues, and preferably at least 1 but not more than about 3 residues, and polyethylene glycol (PEG) chains of the same length.

The amino acid residue(s) that constitute the peptide linker used in conjugating the peptide and the biologically active substance are preferably residues that have no charge and a small molecular size, such as a glycine residue. Further, a sequence that imparts freedom of rotation of the two bonded domains (the biologically active substance and the peptide) is preferably provided at the terminus, and preferably at both termini, of the linker sequence. Specifically, in order to impart freedom of rotation, a sequence containing glycine (G) and containing proline (P) as a linker is preferred, and more specifically, a sequence composed solely of glycine residues and a proline residue, for example, glycine (G)-proline (P)-glycine (G), is particularly preferred. By using such a configuration, the functions of both domains can be realized. Alternatively, in terms of facilitating formation of covalent bonds, the termini of the linker sequence preferably include cysteine (C) or lysine (K). The biologically active substance can then be bonded to the peptide via the thiol group (—SH) of the cysteine residue or the side chain of the lysine residue.

In those cases where the biologically active substance is a protein, when conjugating the biologically active substance and the peptide, the conjugate may be prepared as a fusion protein. Although there are no particular limitations on the position at which the peptide is provided, it is preferable that the peptide is presented outside the protein and has little effect on the activity and functionality of the fusion protein, and is preferably fused at the N-terminus or the C-terminus of the protein that represents the biologically active substance. Although there are no particular limitations on the type of protein that is fused, because drugs that have a molecular weight that is too large are inhibited in terms of passage through the cell membrane, the molecular weight is, for example, typically not more than about 500,000, and may be restricted to not more than about 30,000.

The protein used as the biologically active substance may be an antibody. Such antibodies can be prepared, for example, by immunizing a rodent animal such as a mouse with a peptide or the like derived from a cancer (and particularly a scirrhous carcinoma) as an antigen. Further, antibodies may also be prepared, for example, by screening of a phage library. The antibody may be an antibody fragment, and examples of such antibody fragments include Fv, Fab, and scFv and the like.

Examples of nucleic acids that may be used as the biologically active substance include siRNA, miRNA, antisense, or artificial nucleic acids or the like that compensate for these functions.

Aptamers that may be used as the biologically active substance are substances having a specific binding ability to CAF or cancer stroma. Examples of aptamers include nucleic acid aptamers and peptide aptamers. Nucleic acid aptamers having a specific binding ability to CAF or cancer stroma can be selected, for example, by the systematic evolution of ligand by exponential enrichment (SELEX) method. Peptide aptamers having a specific binding ability to CAF or cancer stroma can be selected, for example, by the two-hybrid method using yeast.

Furthermore, in the PDC of the present embodiment, the peptide may be modified using a modulator in the manner described above, and may also incorporate a labeling substance.

<<Pharmaceutical Composition>>

A pharmaceutical composition of an embodiment of the present invention contains the PDC described above.

The pharmaceutical composition of this embodiment can be used to selectively treat scirrhous carcinoma by targeting the cancer stroma that develops abundantly in invasive pancreatic ductal adenocarcinoma and poorly differentiated stomach adenocarcinoma and the like.

<Composition Components>

The pharmaceutical composition of the present embodiment contains a therapeutically effective amount of the above PDC, and a pharmaceutically acceptable carrier or diluent. Pharmaceutically acceptable carriers or diluents include excipients, extenders, disintegrants, stabilizers, preservatives, buffers, emulsifiers, fragrances, colorants, sweeteners, thickeners, flavoring agents, and solubilizers and the like. By using one or more of these carriers or diluents, pharmaceutical compositions in the form of injections, solutions, capsules, suspensions, emulsions, and syrups and the like can be prepared.

Further, a colloidal dispersion system can also be used as the carrier. Colloidal dispersion systems can be expected to have an effect in enhancing the in vivo stability of the peptide or the PDC, and an effect in enhancing the transferability of the peptide or the PDC into the CAF or cancer stroma. Examples of colloidal dispersion systems include polyethylene glycol, polymer composites, polymer aggregates, nanocapsules, microspheres, beads, oil-in-water emulsifiers, micelles, mixed micelles, and lipids containing liposomes, and among these, liposomes and artificial membrane vesicles, which are effective in efficiently transporting the peptide or the PDC into the CAF or cancer stroma, are preferred.

Examples of the formulation for the pharmaceutical composition of the present embodiment include oral formulations such as tablets which may be sugar-coated as necessary, capsules, elixirs, and microcapsules.

Other examples include parenteral formulations in the form of sterile solutions with either water or another pharmaceutically acceptable liquid, or injectable suspensions.

Moreover, formulations may also be prepared by appropriate combination with a pharmaceutically acceptable carrier or diluent, specifically a vehicle (such as sterilized water, physiological saline, or vegetable oil), or an emulsifier, suspension, surfactant, stabilizer, flavoring agent, excipient, preservative or binder or the like, and then mixing with a unit dosage form typically required in pharmaceutical practice.

Examples of carriers or diluents that may be mixed into tablets or capsules include binders, excipients, swelling agents, lubricants, sweeteners, and flavoring agents. Examples of the binders include gelatin, corn starch, tragacanth gum and gum arabic. Examples of the excipients include crystalline cellulose and the like. Examples of the swelling agents include corn starch, gelatin and alginic acid. Examples of the lubricants include magnesium stearate and the like. Examples of the sweeteners include sucrose, lactose, and saccharin. Examples of the flavoring agents include peppermint refined oil, akamono oil and cherry flavoring. When the dispensed unit form is a capsule, the above material may further contain a liquid carrier such as an oil or fat.

Sterile compositions for injection can be formulated according to normal pharmaceutical practice using a vehicle such as distilled water for injection.

Examples of aqueous solution vehicles for injection include isotonic solutions containing physiological saline, glucose and other adjuvants, and suitable solubilizers and nonionic surfactants and the like may also be added. Examples of the other adjuvants include D-sorbitol, D-mannose, D-mannitol, and sodium chloride. Examples of the solubilizers include alcohols. Specific examples of the alcohols include ethanol and polyalcohols. Examples of these polyalcohols include propylene glycol and polyethylene glycol. Examples of the nonionic surfactants include Polysorbate 80 (a registered trademark) and HCO-50.

Examples of vehicles for non-aqueous solutions for injection include sesame oil and soybean oil, which may be used in combination with benzyl benzoate or benzyl alcohol as a solubilizer. Further, buffering agents, soothing agents, stabilizers, and antioxidants and the like may also be blended into the oil-based solution for injection. Examples of the buffering agents include a phosphate buffer and a sodium acetate buffer. Examples of the soothing agents include procaine hydrochloride and the like. Examples of the stabilizers include benzyl alcohol and phenol. The prepared injection solution is typically loaded into a suitable ampoule.

In the case of an injection, the injection may be prepared as an aforementioned aqueous or non-aqueous solution, suspension, or emulsion. Sterilization of these types of injections can be performed by filtration sterilization using a filter, or by the addition of an antimicrobial agent or the like. Injections can be produced in forms that are prepared at the time of use. In other words, the formulation can be produced as a sterile solid composition by freeze drying or the like, and then dissolved in distilled water for injection or another vehicle prior to use.

<Dosage>

The pharmaceutical composition of the present embodiment is prepared appropriately with due consideration of the type of biologically active substance included in the PDC, and factors such as the age, gender, weight, symptoms, treatment method, administration method and treatment time of the test subject (any of various mammals including humans and non-human animals, but preferably a human).

For example, when the pharmaceutical composition of the present embodiment is injected intravenously (i.v.) using an injection, at least 0.1 mg but not more than about 1,000 mg of the PDC may be administered in a single administration per 1 kg of body weight of the test subject (preferably a human).

Examples of the dosage form include intraarterial injections, intravenous injections, subcutaneous injections, as well as administration by intranasal, intraperitoneal, transbronchial, intramuscular, transdermal, or oral methods known to those skilled in the art, although intravenous injection or intraperitoneal administration is preferred.

<Treatment Method>

In one embodiment, the present invention provides a pharmaceutical composition containing the PDC described above, which is used for the treatment or prevention of cancer (and particularly scirrhous carcinoma). The peptide contained in the PDC causes the drug to accumulate in the CAF or MSC, meaning the greatest effect can be expected for scirrhous carcinoma, but the composition may be used to target any carcinoma containing CAF.

Further, in one embodiment, the present invention provides a pharmaceutical composition containing a therapeutically effective amount of the above PDC and a pharmaceutically acceptable carrier or diluent.

Furthermore, in one embodiment, the present invention provides use of the PDC described above for producing a pharmaceutical composition for the treatment or prevention of cancer (and particularly scirrhous carcinoma).

Furthermore, in one embodiment, the present invention provides a treatment method or prevention method for cancer (and particularly scirrhous carcinoma) that includes administering an effective amount of the PDC described above to a patient requiring treatment.

<<Labeled Peptide>>

A labeled peptide of an embodiment of the present invention contains the peptide described above and a labeling substance.

Examples of the labeling substance include biotin, avidin, streptavidin, stable isotopes, radioisotopes, fluorescent substances, positron emission tomography (PET) nuclides, single photon emission computed tomography (SPECT) nuclides, magnetic resonance imaging (MRI) contrast agents, computed tomography (CT) contrast agents, and magnetic substances. Further, in those cases where the labeling substance is a protein, a nucleic acid that encodes these substances may be used. Among the various options, a stable isotope, a radioisotope, or a fluorescent substance is preferred. By including the labeling substance, a determination as to whether or not the target substance has been delivered to the cancer stroma containing CAF or MSC can be made simply and with high sensitivity.

Examples of stable isotopes include $^{13}C$ (carbon 13), $^{15}N$ (nitrogen 15), $^2H$ (hydrogen 2), $^{17}O$ (oxygen 17) and $^{18}O$ (oxygen 18). Examples of radioisotopes include $^3H$ (hydrogen 3), $^{14}C$ (carbon 14), $^{13}N$ (nitrogen 13), $^{18}F$ (fluorine 18), $^{32}P$ (phosphorus 32), $^{33}P$ (phosphorus 33), $^{35}S$ (sulfur 35), $^{67}Cu$ (copper 67), $^{99m}Tc$ (technetium 99m), $^{123}I$ (iodine 123), $^{131}I$ (iodine 131), $^{133}Xe$ (xenon 133), $^{201}Tl$ (thallium 201), and $^{67}Ga$ (gallium 67). In those cases where the labeling substance is a stable isotope or a radioisotope, the peptide may be prepared using a stable isotope-labeled amino acid or a radioisotope-labeled amino acid. Examples of the amino acid labeled with the stable isotope or radioisotope include the 20 types of amino acids (alanine, arginine, aspartic acid, glutamic acid, glycine, histidine, isoleucine, leucine, lysine, methionine, phenylalanine, proline, serine, threonine, tyrosine, valine, tryptophan, cysteine, asparagine, and glutamine), and any of the amino acids included in the peptide may be labeled without any particular limitations. Further, the amino acid may be an L-form or a D-form, and may be selected appropriately as required In those cases where the labeling substance is a stable isotope or a radioisotope, the labeled peptide may be prepared using a stable isotope-labeled amino acid or a radioisotope-labeled amino acid. In other words, in the labeled peptide of the present embodiment, the expression "contains the peptide described above and a labeling substance" includes the case of a peptide produced using a stable isotope-labeled amino acid or a radioisotope-labeled amino acid.

There are 20 types of amino acids that may be labeled with a stable isotope or a radioisotope (alanine, arginine, aspartic acid, glutamic acid, glycine, histidine, isoleucine, leucine, lysine, methionine, phenylalanine, proline, serine, threonine, tyrosine, valine, tryptophan, cysteine, asparagine, and glutamine), and any of the amino acids included in the peptide may be labeled without any particular limitations. Further, the amino acid may be an L-form or a D-form, any may be selected appropriately as required.

The labeled peptide of the present embodiment produced using a stable isotope-labeled amino acid or a radioisotope-labeled amino acid can be prepared by expressing a vector containing the nucleic acid that encodes the peptide in a system in which a stable isotope-labeled amino acid or a radioisotope-labeled amino acid is present. Examples of systems in which a stable isotope-labeled amino acid or a radioisotope-labeled amino acid is present include cell-free peptide synthesis systems and living cell peptide synthesis systems in which a stable isotope-labeled amino acid or a radioisotope-labeled amino acid is present. In other words, by synthesizing the peptide in a cell-free peptide synthesis system using a stable isotope-unlabeled amino acid(s) or radioisotope-unlabeled amino acid(s) as well as the stable isotope-labeled amino acid or radioisotope-labeled amino acid, or in the case of a living cell peptide synthesis system, by culturing cells that have been transformed by a vector containing a nucleic acid that encodes the peptide in the presence of a stable isotope-labeled amino acid or a radioisotope-labeled amino acid, a peptide that has been labeled with the stable isotope or the radioisotope can be prepared from the vector containing the nucleic acid that encodes the peptide.

Production of the labeled peptide of the present embodiment using a cell-free peptide synthesis system can be conducted using, besides the vector containing a nucleic acid that encodes the peptide and the aforementioned stable isotope-labeled amino acid or radioisotope-labeled amino acid, any stable isotope-unlabeled amino acids or radioisotope-unlabeled amino acids required for the synthesis of the peptide labeled with the stable isotope or radioisotope, a cell extract for cell-free peptide synthesis, and an energy source (a high-energy phosphate bond-containing material such as ATP, GTP or creatine phosphate). The reaction conditions such as the temperature and time may be selected as appropriate, and for example, the temperature may be set to at least 20° C. but not more than 40° C., and preferably at least 23° C. but not more than 37° C. Further, the reaction time may be set to at least 1 hour but not more than 24 hours, and is preferably at least 10 hours but not more than 20 hours.

In this description, the term "cell extract for cell-free peptide synthesis" means an extract from plant cells, animal cells, fungal cells or bacterial cells that contains components required for a translation system, or a transcription system and translation system, that participates in the synthesis of proteins such as ribosomes or tRNA. Specific examples include cell extracts of E. coli, wheat germ, rabbit reticulocytes, mouse L-cells, Ehrlich ascites tumor cells, HeLa cells, CHO cells, and budding yeast. Preparation of these cell extracts may be performed, for example, in accordance with the method described in Pratt, J M. et al., Transcription and Translation—A Practical Approach (1984), pp. 179 to 209, by disrupting the above cells using a French press, glass beads, or an ultrasonic disruptor or the like, adding a buffer containing several types of salts to solubilize the protein components and ribosomes, homogenizing the resulting mixture, and then precipitating the insoluble components by centrifugal separation.

Furthermore, expression of the aforementioned peptide that has been labeled with a stable isotope or a radioisotope using a cell-free peptide synthesis system may also be conducted by appropriate use of a commercially available kit such as a Premium Expression Kit with a wheat germ extract (manufactured by CellFree Sciences Co., Ltd.), an RTS 100, an E. coli HY Kit with an E. coli extract (manufactured by Roche Applied Science, Inc.), or a cell-free Quick (manufactured by Taiyo Nippon Sanso Corporation).

In those cases where the expressed stable isotope-labeled or radioisotope-labeled peptide is insoluble, the peptide may be solubilized appropriately using a protein denaturant such as guanidine hydrochloride or urea. The stable isotope-labeled or radioisotope-labeled peptide can then be prepared by purification by a fractionation treatment using a fractional centrifugation method or sucrose density gradient centrifugation method or the like, or by affinity column purification or ion exchange chromatography.

Production of the labeled peptide of the present embodiment using a living cell peptide synthesis system can be conducted by introducing a vector containing a nucleic acid that encodes the peptide into the living cells, and then culturing the living cells in a culture solution containing nutrients and an antibiotic and the like as well as the aforementioned stable isotope-labeled amino acid or radioisotope-labeled amino acid, and any stable isotope-unlabeled amino acids or radioisotope-unlabeled amino acids required for the synthesis of the stable isotope-labeled peptide or radioisotope-labeled peptide. There are no particular limitations on the living cells, provided they are living cells capable of expressing the vector containing the nucleic acid that encodes the peptide, and examples include mammalian cell lines such as Chinese hamster ovary (CHO) cells, E. coli, yeast cells, insect cells and plant cells, and if consideration is given to simplicity and cost effectiveness, then E. coli is preferred. Expression of the vector containing the nucleic acid that encodes the above peptide can be performed by using gene recombination technology to assemble an expression vector designed to be capable of expression in the selected living cells, and then introducing that expression vector into the living cells. Further, the introduction into living cells of the vector containing the nucleic acid that encodes the peptide may be conducted using a method suited to the living cells being used, such as an electroporation method, heat shock method, calcium phosphate method, lipofection method, DEAE dextran method, microinjection method, particle gun method, a method using a virus, or a method using a commercially available transfection reagent such as FuGENE (a registered trademark) 6 Transfection Reagent (manufactured by Roche Holding AG), Lipofectamine 2000 Reagent (manufactured by Invitrogen Corporation), Lipofectamine LTX Regent (manufactured by Invitrogen Corporation), or Lipofectamine 3000 Reagent (manufactured by Invitrogen Corporation).

The stable isotope-labeled or radioisotope-labeled peptide expressed by a living cell peptide synthesis system can be prepared by disruption and extraction of the living cells containing the stable isotope-labeled or radioisotope-labeled peptide. Examples of the disruption treatment include physical disruption treatments using a freeze-thaw method, a French press, glass beads, a homogenizer, or an ultrasonic disruptor or the like. Further, examples of the extraction treatment include extraction treatments using a protein denaturant such as guanidine hydrochloride or urea. The stable isotope-labeled or radioisotope-labeled peptide can then be prepared by purification by a fractionation treatment using a fractional centrifugation method or sucrose density gradient centrifugation method or the like, or by affinity column purification or ion exchange chromatography.

Examples of the fluorescent substance include conventional quantum dots, indocyanine green, 5-aminolevulinic acid (5-ALA; metabolite protoporphyrin IX (PP IX)), near-infrared (NIR) fluorescent dyes (such as Cy5.5, Cy7, and AlexaFluoro), and other known fluorescent dyes (such as GFP, FITC (Fluorescein), FAM and TAMRA). In those cases where the fluorescent substance is a protein, the fluorescent substance-labeled peptide described above may be obtained by preparing a vector containing a nucleic acid that encodes the fluorescent substance and a nucleic acid that encodes the peptide in either an aforementioned cell-free peptide synthesis system or a living cell peptide synthesis system without using a stable isotope-labeled amino acid or radioisotope-labeled amino acid.

Examples of preferred PET nuclides and SPECT nuclides include $^{11}$C, $^{13}$N, $^{15}$O, $^{18}$F, $^{66}$Ga, $^{67}$Ga, $^{68}$Ga, $^{60}$Cu, $^{61}$Cu, $^{62}$Cu, $^{67}$Cu, $^{64}$Cu, $^{48}$V, Tc-99m, $^{241}$Am, $^{55}$Co, $^{57}$Co, $^{153}$Gd, $^{111}$In, $^{133}$Ba, $^{82}$Rb, $^{139}$Ce, Te-123m, $^{137}$Cs, $^{86}$Y, $^{90}$Y, $^{185/187}$Re, $^{186/188}$Re, $^{125}$I, as well as complexes thereof and combinations thereof. The peptide labelled with either a PET nuclide or a SPECT nuclide can be prepared by preparing a vector containing a nucleic acid that encodes the peptide in either an aforementioned cell-free peptide synthesis system or a living cell peptide synthesis system.

Examples of the MRI contrast agent, CT contrast agents and magnetic substances include gadolinium, Gd-DTPA, Gd-DTPA-BMA, Gd-HP-DO3A, iodine, iron, iron oxide, chromium, manganese, or a complex thereof, or chelate complex thereof. The peptide labeled with an MRI contrast agent, CT contrast agent or magnetic substance may be prepared by physically or chemically bonding the MRI contrast agent, CT contrast agent or magnetic substance and the peptide, either directly or via a linker. Specific examples of the bonding method include coordination bonding, covalent bonding, hydrogen bonding, hydrophobic interactions and physical adsorption, and any conventional bonding, linkers or bonding methods may be employed.

<Method for Imaging Cancer Stroma>

A method according to one embodiment of the present invention is a method for imaging cancer stroma containing CAF or MSC, and uses the labeled peptide described above.

Further, an imaging composition of an embodiment of the present invention contains the labeled peptide described above. In other words, am imaging composition of an embodiment of the present invention can be used as an imaging agent for cancer stroma containing CAF or MSC.

By using the method and the imaging composition of these embodiments, cancer stroma containing CAF or MSC can be detected simply, and with high sensitivity and selectivity.

<Composition Components>

The imaging composition of an embodiment of the present invention contains the labeled peptide described above, and may also contain a pharmaceutically acceptable carrier or diluent as required. Examples of the pharmaceutically acceptable carrier or diluent include conventional components typically used in imaging compositions among those components exemplified above for the aforementioned pharmaceutical composition.

The method and the imaging composition of these embodiments may also use, in addition to the labeled peptide described above, a peptide having a high degree of accumulation in the cancer cells or cancer tissue of various cancers composed mainly of a scirrhous carcinoma. By also using a peptide having a high degree of accumulation in the cancer cells or cancer tissue of various cancers composed mainly of a scirrhous carcinoma, for example, both the cancer cells and the cancer stroma that constitute a scirrhous carcinoma can be imaged in a single process. The peptide having a high degree of accumulation in the cancer cells or cancer tissue of various cancers composed mainly of a scirrhous carcinoma may be modified with a modulator. In those cases where the peptide having a high degree of accumulation in the cancer cells or cancer tissue of various cancers composed mainly of a scirrhous carcinoma includes a labeling substance, the labeling substance is preferably of a different type from the labeling substance of the peptide having a high degree of accumulation in CAF. By using labeling substances of different types, simultaneous imaging can be conducted while differentiating between cancer cells and CAF.

For example, in those cases where the labeled peptide described above is added to CAF, the amount added of the labeled peptide is preferably at least 1 µM but not more than 10 µM within the culture solution. Further, an evaluation as to whether or not the labeled peptide has been absorbed and accumulated in the CAF may be conducted at least 15 minutes but not more than 3 hours after the addition of the peptide.

Further, in those cases where, for example, a labeled peptide containing a fluorescent substance as the labeling substance is injected intravenously (i.v.) with an injection, the labeled peptide may be administered, for example, in an amount of at least 0.1 mg but not more than about 1,000 mg in a single administration per 1 kg of body weight of the test subject (preferably a human), and the labeled peptide is preferably administered in an amount of at least 3 mg but not more than 1,000 mg, more preferably an amount of at least 3 mg but not more than 20 mg, and even more preferably an amount of at least 5 mg but not more than 15 mg.

Furthermore, in those cases where, for example, a labeled peptide containing a stable isotope, a PET nuclide or a SPECT nuclide as the labeling substance is injected intravenously (i.v.) with an injection, the administered dosage may be determined from the radiation dose in accordance with the stable isotope, PET nuclide or SPECT nuclide that is used.

In the method of an embodiment of the present invention, examples of the method used for detecting the labeled peptide include PET, SPECT, CT, MRI, detection by endoscope, and detection using a fluorescence detector.

The method and the imaging composition of embodiments of the present invention can be used for diagnosis, pathological analysis, treatment, or analysis of treatment efficacy for scirrhous carcinoma or diseases associated with scirrhous carcinoma.

EXAMPLES

The present invention is described below using a series of examples, but the present invention is not limited by the following examples.

Example 1

(Identification of Peptides Having Penetration into Human Mesenchymal Stem Cells)

Using an independently prepared 9-amino acid residue peptide as a phenotype linked via puromycin to a protein-RNA chimeric random peptide library (in vitro virus library; IVVL) having an mRNA coding sequence as the corresponding genotype, a conventional IVV (in vitro virus) method was used with human mesenchymal stem cells (hMSC) as the absorption target cells to repeat a reaction cycle in a culture system, thus isolating 81 types of peptide having penetration into mesenchymal stem cells (mesenchymal stem cell-penetrating peptide; MSCPP).

Next, fusion peptides (having a His tag formed from six histidine residues at the C-terminus of the fusion peptide) of each of the 81 isolated MSCPP and EGFP (excitation wavelength: 488 nm, fluorescence wavelength: 509 nm) (MSCPP-EGFP$_{HIS}$) were produced. The penetration properties into hMSC were evaluated for each of the MSCPP-EGFP$_{HIS}$. Cells of the hMSC line UE6E7T-3 were used as the hMSC. An RPMI 1640 medium containing 10% FBS was used as the medium. The UE6E7T-3 cells were inoculated into a 96-well plate, medium containing each MSCPP-EGFP$_{HIS}$ (5 μL of fusion peptide solution and 50 μL of medium per well) was added, and the mixtures were cultured for four hours. Following culturing, the cells were inspected under a fluorescence microscope. Representative results are shown in FIG. 1. In FIG. 1, "EGFP$_{HIS}$" represents EGFP having a His tag formed from six histidine residues at the C-terminus, but not being fused with an MSCPP peptide. Further, "Poly-r9" (9-residue continuous D-arginine) is a non-selective membrane-permeable peptide that is currently widely used.

Furthermore, the amino acid sequences of the various MSCPP shown in FIG. 1 are shown below in Table 1.

TABLE 1

| Name | Sequence (5' → 3') | SEQ ID NO: |
|---|---|---|
| Poly-r9 | RRARRARRR | 12 |
| MSCPP13 | RARVAWDWI | 13 |
| MSCPP22 | WTRTQWPLH | 14 |
| MSCPP33 | WPPLQRWRN | 2 |
| MSCPP48 | RTHPVWSRT | 3 |
| MSCPP49 | RRWMQWPWH | 4 |
| MSCPP106 | KCAELFRHL | 1 |

Based on FIG. 1, it was confirmed that the four peptides MSCPP33, 48, 49 and 106 exhibited penetration into human bone marrow-derived mesenchymal stem cells (hMSC). Particularly strong fluorescence was observed for MSCPP106.

Example 2

(Cell Selectivity of Peptides)

Among the peptides identified in Example 1, the four peptides MSCPP33, 48, 49 and 106, Poly-r9 as a positive control and MSCPP22 as a negative control were synthesized with an FITC (fluorescein isothiocyanate) (excitation wavelength: 495 nm, fluorescence wavelength: 520 nm) label, and then subjected to a hydrochloride treatment. These peptides were each obtained via contract synthesis by Sigma-Aldrich Japan (Genosis division). The MSCPP33 was dissolved in 20% DMSO. The MSCPP48 developed a precipitate following thawing of the frozen state, and was therefore subjected to a sonication treatment prior to use. The MSCPP49 and MSCPP106 were dissolved in water prior to use.

Figure 2:
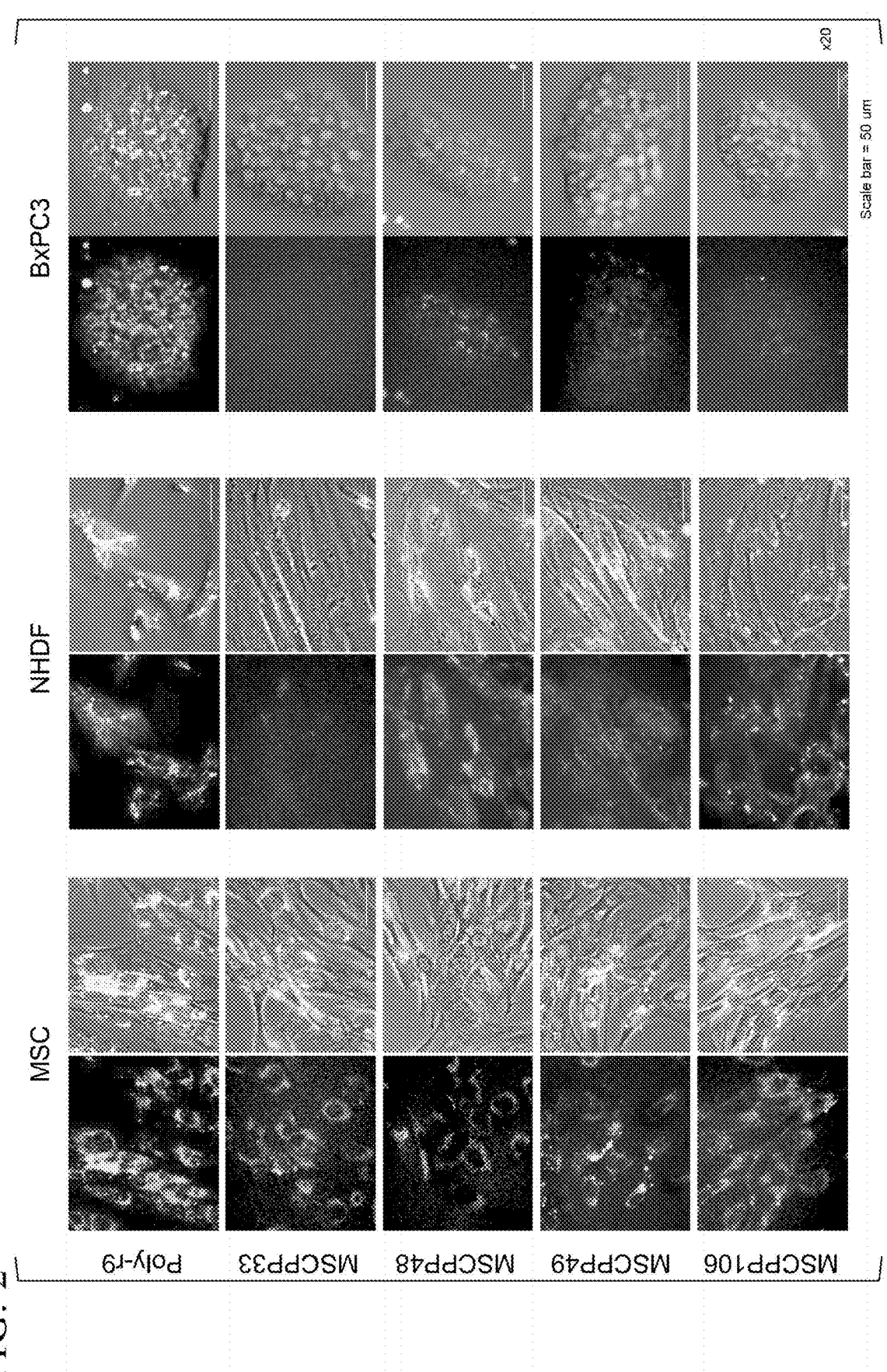
FIG. 2 is a series of fluorescent images (left) and merged images of a fluorescent image and a phase difference microscope image (right) of various cells to which various peptides have been added in Example 2. The scale bars indicate 50 μm.

Subsequently, the penetration of each peptide into hMSC, normal human dermal fibroblasts (NHDF), and BxPC3 cells, which are an established cell line derived from human pancreatic adenocarcinoma, was confirmed. In the case of the hMSC, cells that had been inoculated into a 24-well plate at 4×10⁴ cells/well and then cultured for 24 hours in an MSC medium were used. In the case of the NHDF and BxPC3 cells, cells that had been inoculated into a 24-well plate at 4×10⁴ cells/well and then cultured for 24 hours in an RPMI 1640 medium containing 10% FBS were used. Mediums (RPMI 1640 medium containing 10% FBS) containing 4 μM of each of the peptides were then added to each of the cells and cultured for four hours. Following culturing, each of the cells was subjected to nuclear staining with Hoechst 33342 (excitation wavelength: 352 nm, fluorescence wavelength: 461 nm), and was then observed using a phase difference/fluorescence microscope. The results are shown in FIG. 2. In FIG. 2, the images shown on the left side are FITC fluorescence images, and the images shown on the right side are merged images of the fluorescence image and the phase difference microscope image.

Based on FIG. 2, it was confirmed that the four peptides MSCPP33, 48, 49 and 106 all exhibited high absorption and fixed selective absorption into hMSC. In a similar manner to Example 1, MSCPP106 represents an example of an ideal peptide that simultaneously exhibits the following three properties, namely, efficient absorption into hMSC, low absorption into the pancreatic cancer cells BxPC3, and lower absorption into NHDF compared with the absorption into hMSC. Accordingly, MSCPP106 was used in the following tests.

Example 3

(Absorption of MSCPP106 into CAF)

Figure 3:
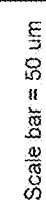
FIG. 3 is a series of fluorescent images and phase difference microscope images of various cells to which FITC-MSCPP106 has been added in Example 3. The scale bars indicate 50 μm.

Using the FITC-MSCPP106 produced in Example 2, the absorption into CAF was confirmed in a coculture system of pancreatic cancer cells and MSC. Specifically, BxPC3 cells and hMSC (a cell line expressing DsRed2) were each inoculated into a 24-well plate at 4×10⁴ cells/well, and four hours after the inoculation, the medium was replaced with an RPMI medium containing 10% FBS, and culturing was conducted for 60 hours. In the case of the coculture of BxPC3 cells and hMSC, each of the cells was inoculated into a 24-well plate at a ratio of 1:1 to achieve a total cell count of 4×10⁴ cells/well (each cell: 2×10⁴ cells/well), and four hours after the inoculation, the medium was replaced with an RPMI medium containing 10% FBS, and culturing was conducted for 60 hours. In the case of hMSC, the cells were inoculated into a 24-well plate at 4×10⁴ cells/well, and four hours after the inoculation, the medium was replaced with an MSC medium, and culturing was conducted for 60 hours. Following culturing, a medium (RPMI 1640 medium containing 10% FBS) containing 4 μM of FITC-MSCPP106 was added to each of the cells, and cultured for four hours. Following culturing, each of the cells was subjected to nuclear staining with Hoechst 33342 (excitation wavelength: 352 nm, fluorescence wavelength: 461 nm), and was then observed using a phase difference/fluorescence microscope. The results are shown in FIG. 3. In FIG. 3, "Merge" indicates merged images of the FITC fluorescence image and the DsRed2 fluorescence image, and "Phase" indicates phase difference microscope images. In the following tests, "Phase" similarly indicates phase difference microscope images.

Based on FIG. 3, it was evident that FITC-MSCPP106 exhibited absorption into both hMSC that had been cultured in the RPMI 1640 medium containing 10% FBS, and hMSC that had been cultured in the MSC medium. Moreover, in the mixed culture of BxPC3 cells and hMSC, the hMSC altered to an elongated fibroblast-like shape, indicating the possibility of differentiation into CAF. It was also clear that in this mixed culture of BxPC3 cells and hMSC, the FITC-MSCPP106 was absorbed selectively into only the hMSC. Following approximately 48 hours of coculture with the pancreatic cancer cells, the hMSC exhibited strong expression of the CAF selective cell marker FAPα (fibroblast activating protein α), and displayed differentiation upon culturing in the presence of fetal bovine serum, confirming the expression of CAF immunophenotype (not shown in the drawings).

Example 4

(Plasma Degradation Resistance of MSCPP106)

For the single peptide, tandem peptide, and tandem mutated peptide of MSCPP106 shown below in Table 2, the degradation resistance in human plasma was investigated. In Table 2, "tandem MSCPP106" describes a peptide composed of sequence containing two repeated amino acid sequences for MSCPP106 linked via a glycine residue spacer. Further, "tandem mut MSCPP106" describes a peptide composed of a sequence in which the cysteine residues in the amino acid sequence of tandem MSCPP106 have been methylated (mC).

TABLE 2

| Name | Sequence (5' → 3') | SEQ ID NO: |
| --- | --- | --- |
| Single MSCPP106 | KCAELFRHL | 1 |
| Tandem MSCPP106 | KCAELFRHL-G-KCAELFRHL | 5 |
| Tandem mut MSCPP106 | KmCAELFRHL-G-KmCAELFRHL | 6 |

Each of the above peptides was added to human plasma with a concentration of 50% by mass, the mixture was then sampled immediately after starting the degradation test (0 minutes), and then after 5 minutes, after 10 minutes, after 20 minutes, after 30 minutes, after 60 minutes and after 120 minutes, and each sample was analyzed by MALDI-TOFMS (Matrix Assisted Laser Desorption/Ionization-Time of Flight Mass Spectrometry). The ratio of the mass of the retained peptide that had not degraded at each of the sampling points from the start of the test, relative to the mass of the peptide (100% by mass) at the start of the test was calculated and graphed (see FIG. 4).

Figure 4:
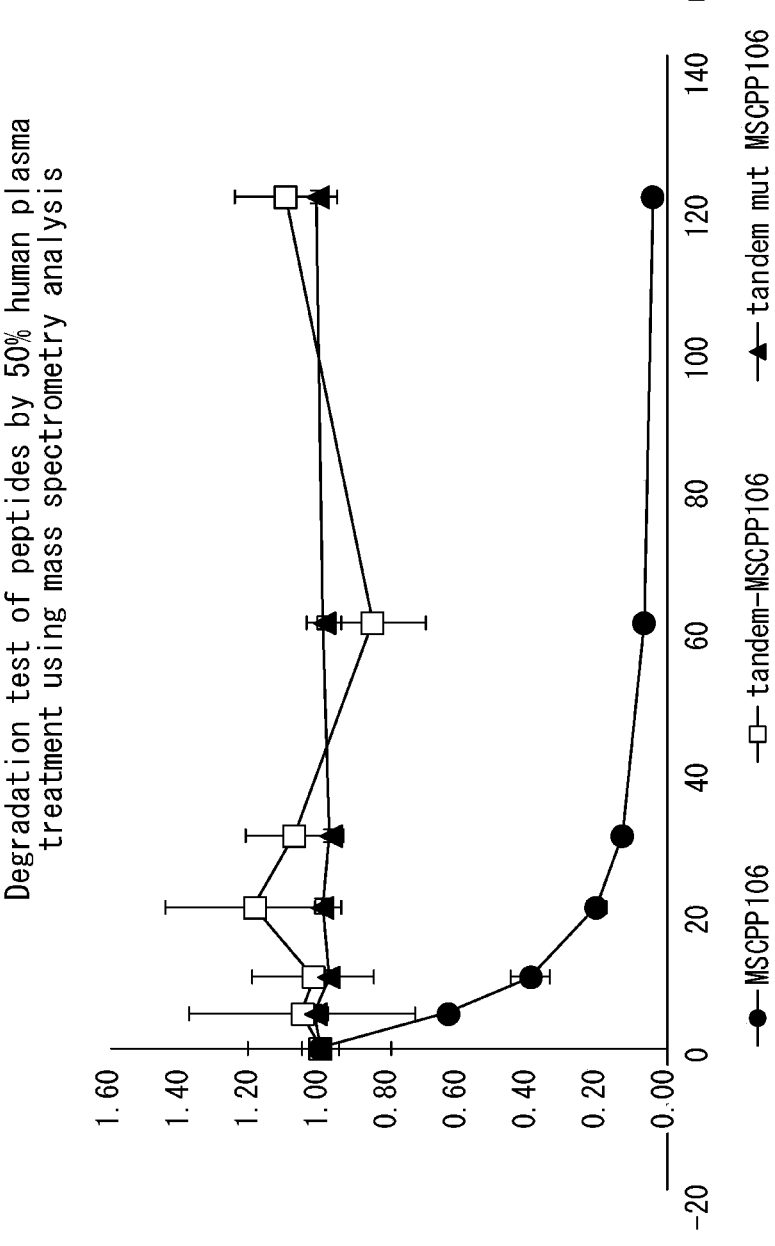
FIG. 4 is a graph comparing the degradation resistance of each of the peptides in Example 4.

Based on FIG. 4, it was ascertained that the tandem MSCPP106 and the tandem mut MSCPP106 exhibited excellent degradation resistance compared with the single MSCPP106.

Based on these results, tandem MSCPP106 was used in the following tests.

Example 5

(Absorption of [FAM]-Tandem MSCPP106 into hMSC in In-Vitro System)

Tandem MSCPP106 was added to a coculture of pancreatic cancer cells and hMSC, and the absorption into the hMSC was investigated. A labeled peptide ([FAM]-tandem MSCPP106) labeled with carboxyfluorescein (FAM) at the N-terminus was used as the tandem MSCPP106. BxPC3 cells and Capan-2 cells, which are a human pancreatic ductal adenocarcinoma cell line, were used as the pancreatic cancer cells. A cell line expressing DsRed2 was used as the hMSC. Specifically, the pancreatic cancer cells and hMSC were each inoculated into a 24-well plate at a ratio of 1:1 to achieve a total cell count of $4\times10^4$ cells/well (each cell: $2\times10^4$ cells/well), and four hours after the inoculation, medium was replaced with an RPMI medium containing 10% FBS, and culturing was conducted for 60 hours.

Figure 5A:
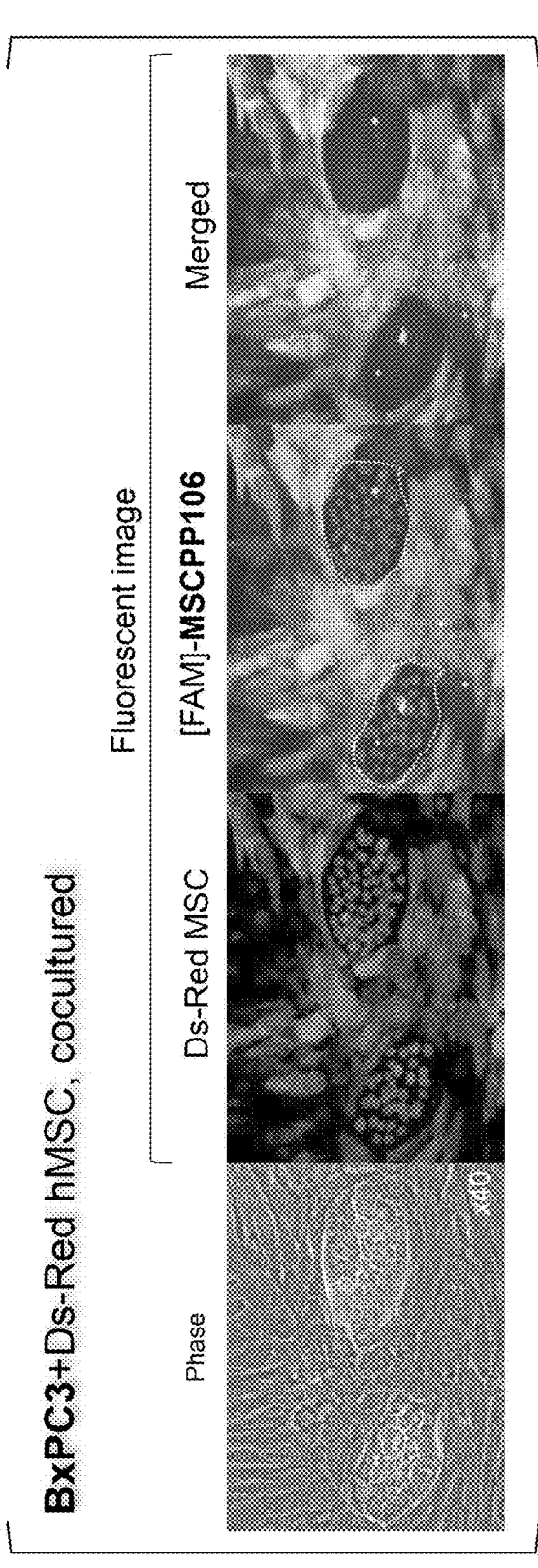
FIG. 5A is a phase difference microscope image and a series of fluorescent images of a cocultured product of BxPC3 cells and hMSC to which [FAM]-tandem MSCPP106 has been added in Example 5.
Figure 5B:
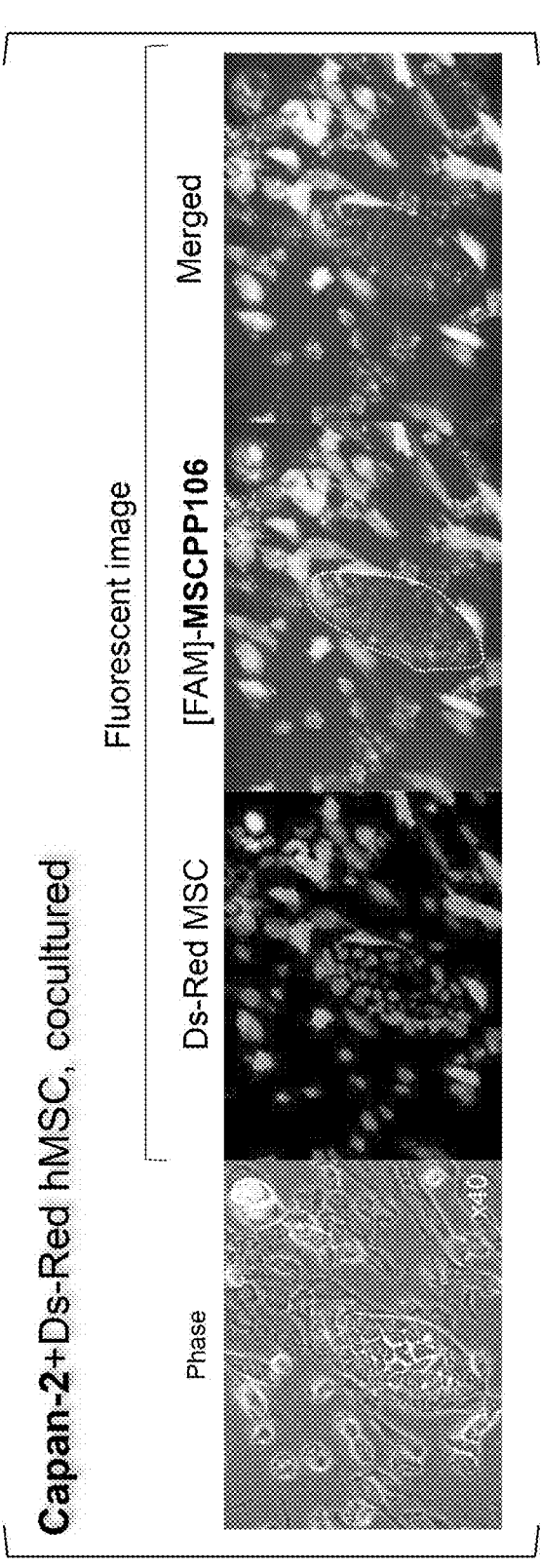
FIG. 5B is a phase difference microscope image and a series of fluorescent images of a cocultured product of Capan-2 cells and hMSC to which [FAM]-tandem MSCPP106 has been added in Example 5.

Following culturing, a medium (RPMI 1640 medium containing 10% FBS) containing 4 µM of [FAM]-tandem MSCPP106 was added to each of the cocultures, and cultured for four hours. Following culturing, each of the cells was subjected to nuclear staining with Hoechst 33342 (excitation wavelength: 352 nm, fluorescence wavelength: 461 nm), and was then observed using a phase difference/fluorescence microscope (magnification: 40×). The results are shown in FIG. 5A (coculture of BxPC3 cells and hMSC) and FIG. 5B (coculture of Capan-2 cells and hMSC). In FIG. 5A and FIG. 5B, "Merge" indicates a merged image of the FAM fluorescence image and the DsRed 2 fluorescence image.

Based on FIG. 5A and FIG. 5B, it was confirmed that, in cocultures of various pancreatic cancer cells and hMSC, [FAM]-tandem MSCPP106 was not absorbed into the pancreatic cancer cells, and was selectively absorbed into only the hMSC.

Example 6

(Intracellular Localization of [FAM]-Tandem MSCPP106)

Figure 6:
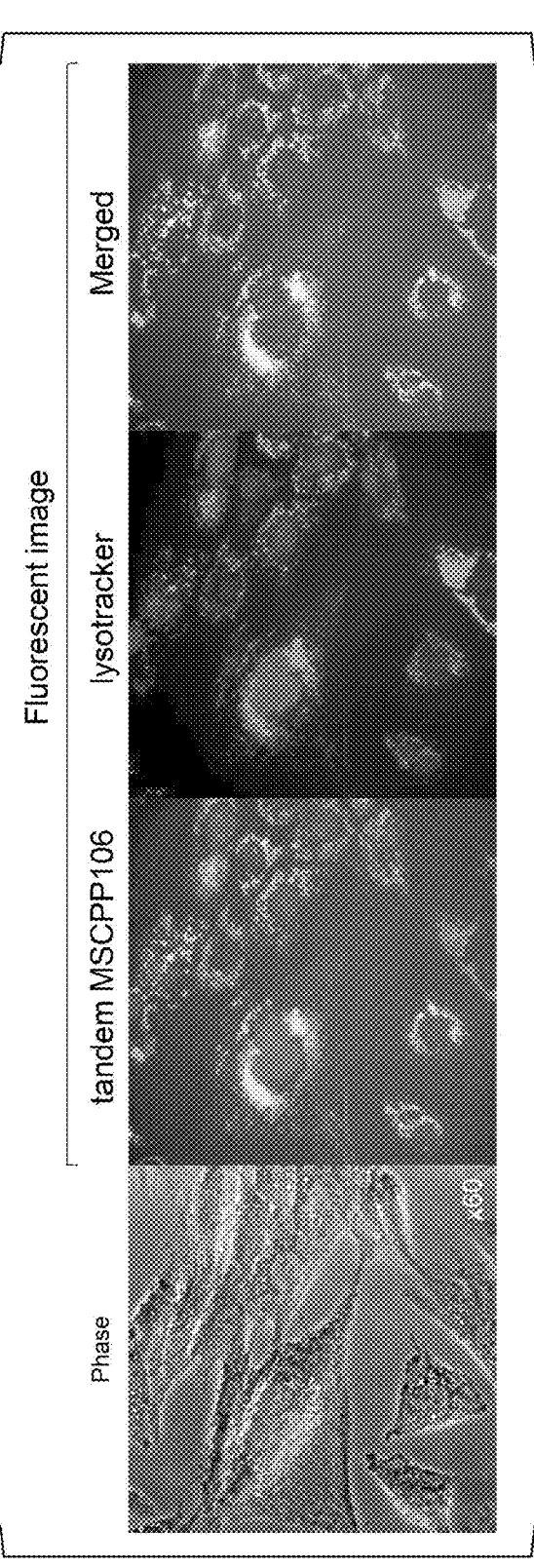
FIG. 6 is a phase difference microscope image and a series of fluorescent images of hMSC to which [FAM]-tandem MSCPP106 has been added in Example 6.

Next, the intracellular localization of [FAM]-tandem MSCPP106 was investigated. Specifically, hMSC were inoculated into a 24-well plate to achieve $4\times10^4$ cells/well, and four hours after the inoculation, the medium was replaced with an RPMI medium containing 10% FBS, and culturing was conducted for 60 hours. Following culturing, a medium (RPMI 1640 medium containing 10% FBS) containing 4 µM of [FAM]-tandem MSCPP106 was added to the hMSC and cultured for 24 hours. Following culturing, nuclear staining was conducted with Hoechst 33342 (excitation wavelength: 352 nm, fluorescence wavelength: 461 nm), lysosomes were also stained using LysoTracker (a registered trademark) RED DND-99 (a lysosome content marker, excitation wavelength: 555 nm, fluorescence wavelength: 584 nm), and the cultures were then observed using a phase difference/fluorescence microscope (magnification: 60×). The results are shown in FIG. 6. In FIG. 6, "Merge" indicates a merged image of the FAM fluorescence image and the LysoTracker (a registered trademark) RED DND-99 fluorescence image.

Based on FIG. 6, it was ascertained that 24 hours after administration, the majority of the tandem MSCPP106 was localized mainly in lysosomes inside the cells. Moreover, the fluorescence of the peptide localized in the lysosomes was detected in a satisfactorily maintained state, indicating that the tandem MSCPP106 has significant resistance to intracellular digestion (degradation) for at least 24 hours.

Example 7

(Selective Absorption of [FAM]-Tandem MSCPP106 in In-Vivo System)

Figure 7A:
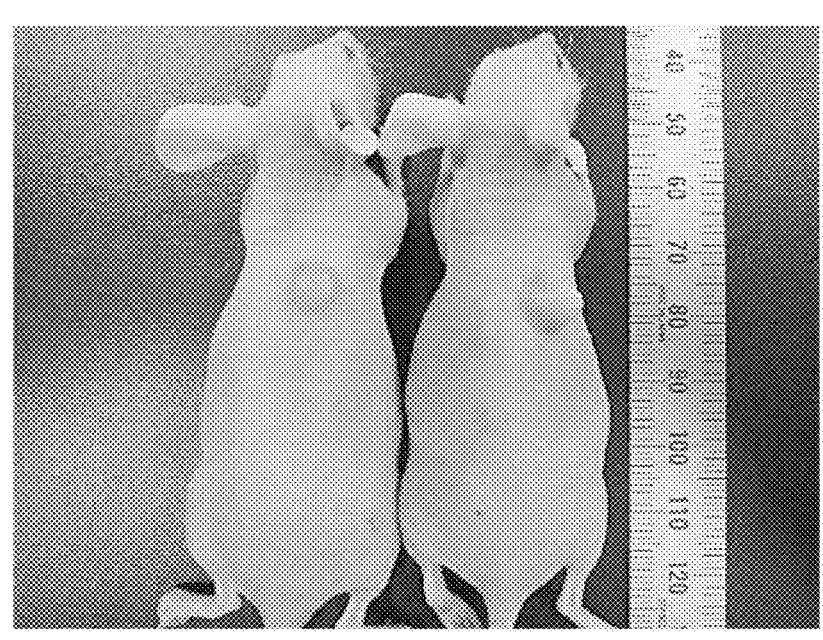
FIG. 7A is a full body image of scirrhous carcinoma model mice in Example 7.

[FAM]-tandem MSCPP106 was administered to a pancreatic cancer model mouse having scirrhous carcinoma, and the selective absorption of the [FAM]-tandem MSCPP106 in various tissues of the mouse was confirmed. A scirrhous pancreatic cancer model mouse having scirrhous carcinoma that forms abundant cancer stroma was produced in accordance with the method disclosed in Reference Document 1 (Saito K et al., "Stromal mesenchymal stem cells facilitate pancreatic cancer progression by regulating specific secretory molecules through mutual cellular interaction.", Journal of Cancer, Vol. 9, No. 16, pp. 2916-2929, 2018). Specifically, 6-week old NOD/SCID mice (CLEA Japan Inc., Japan) were raised under pathogen-free conditions. A cell mixture containing BxPC3 cells ($1 \times 10^5$ cells) and hMSC ($1 \times 10^5$ cells) was injected either subcutaneously or into the abdominal cavity of each mouse. By raising the mice for 6 weeks from the time of cell injection, scirrhous pancreatic cancer model mice were obtained having an abundantly developed cancer stroma that imitates the tissue in a human pancreatic cancer patient (see FIG. 7A).

Figure 7B:
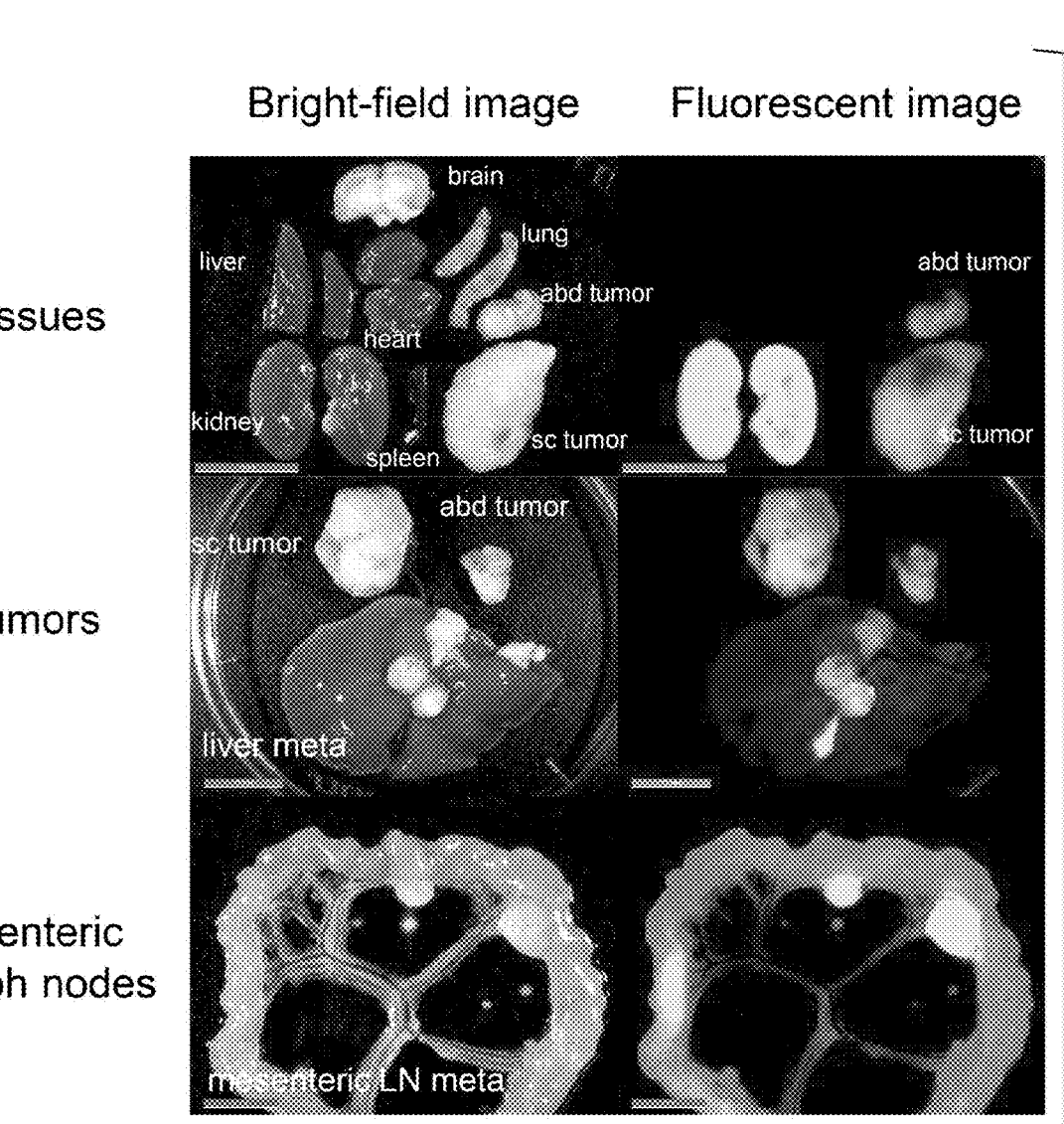
FIG. 7B is a series of bright-field images (left) and fluorescent images (right) of various tissues and various tumor tissues resected from a scirrhous carcinoma model mouse in Example 7.
Figure 7C:
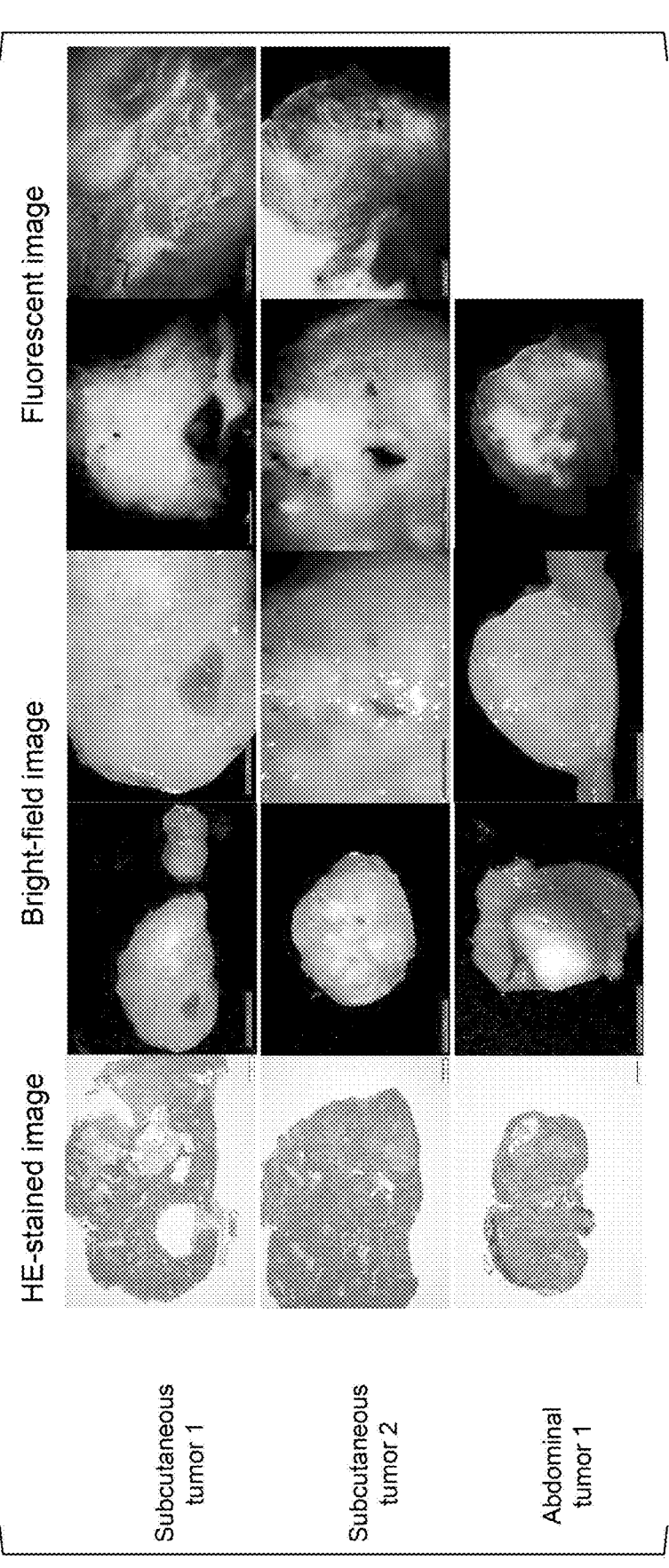
FIG. 7C is a series of hematoxylin-eosin (HE) stained images, bright-field images and fluorescent images of various tumor tissues resected from a scirrhous carcinoma model mouse in Example 7.

[FAM]-tandem MSCPP106 (200 µg) was injected intravenously into each obtained scirrhous carcinoma model mouse. Subsequently, the pharmacokinetics of the peptide 30 minutes after the intravenous injection were analyzed by tissue analysis of the freshly dissected specimen of the peptide-administered mouse. The results are shown in FIG. 7B and FIG. 7C. FIG. 7B is a series of bright-field images (left) and fluorescent images (right) of various tissues and tumor tissues resected from the scirrhous carcinoma model mouse. In FIG. 7B, "abd tumor" is an abbreviation of "abdominal tumor", and refers to a tumor formed in the abdominal cavity. Further, "sc tumor" is an abbreviation of "subcutaneous tumor", and refers to a subcutaneous tumor. Furthermore, "liver meta" is an abbreviation of "liver metastatic tumor", and describes a tumor that has metastasized to the liver. Moreover, "mesenteric LN meta" is an abbreviation of "mesenteric lymph nodes metastatic tumor", and describes a tumor that has metastasized to the mesenteric lymph nodes. FIG. 7C is a series of hematoxylin-eosin (HE) stained images, bright-field images, and fluorescent images of various tumor tissues. In FIG. 7C, the subcutaneous tumor 1 and the subcutaneous tumor 2 are tumors resected from the same dissected specimen.

Based on FIG. 7B and FIG. 7C, it was confirmed that [FAM]-tandem MSCPP106 displayed strong absorption into the cancer stroma (fibrous stroma) that develops inside tumor tissue.

Example 8

(Absorption of [FAM]-Tandem MSCPP106 into CAF in In-Vivo System)

Next, the selective absorption of [FAM]-tandem MSCPP106 into the CAF of cancer stroma was investigated. Using the same method as Example 7, a scirrhous cancer model mouse was obtained. Subsequently, the obtained scirrhous cancer model mouse was injected intravenously with [FAM]-tandem MSCPP106 (300 µg). Subsequently, the pharmacokinetics of the peptide 30 minutes after the intravenous injection were analyzed by tissue analysis of the freshly dissected specimen of the peptide-administered mouse. The results are shown in FIG. 8A to FIG. 8C.

Figure 8A:
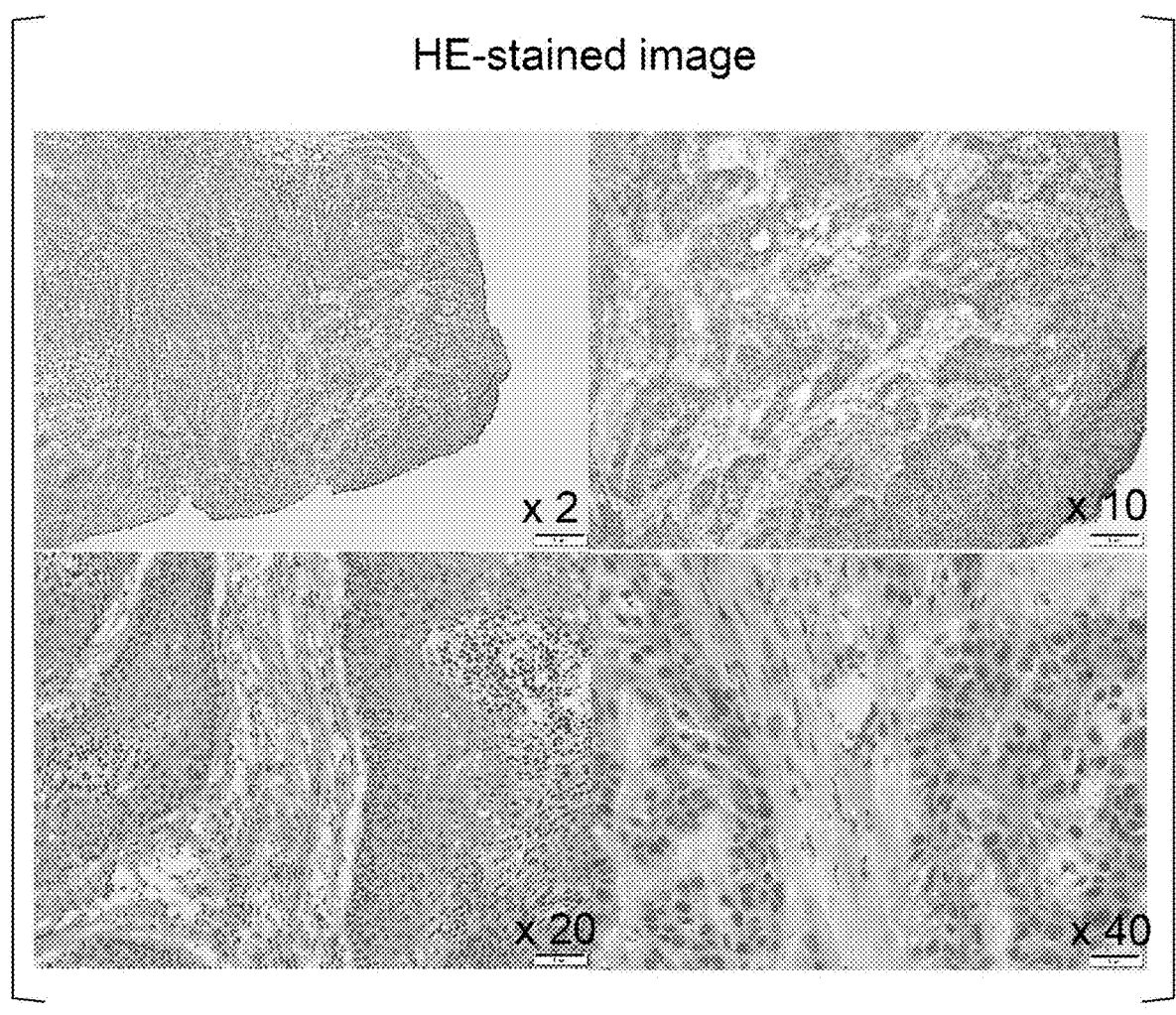
FIG. 8A is a series of HE-stained images of a subcutaneous tumor in a mouse in Example 8.

FIG. 8A is a series of HE-stained images of a subcutaneous tumor (magnification: 2×, 10×, 20× and 40×).

Figure 8B:
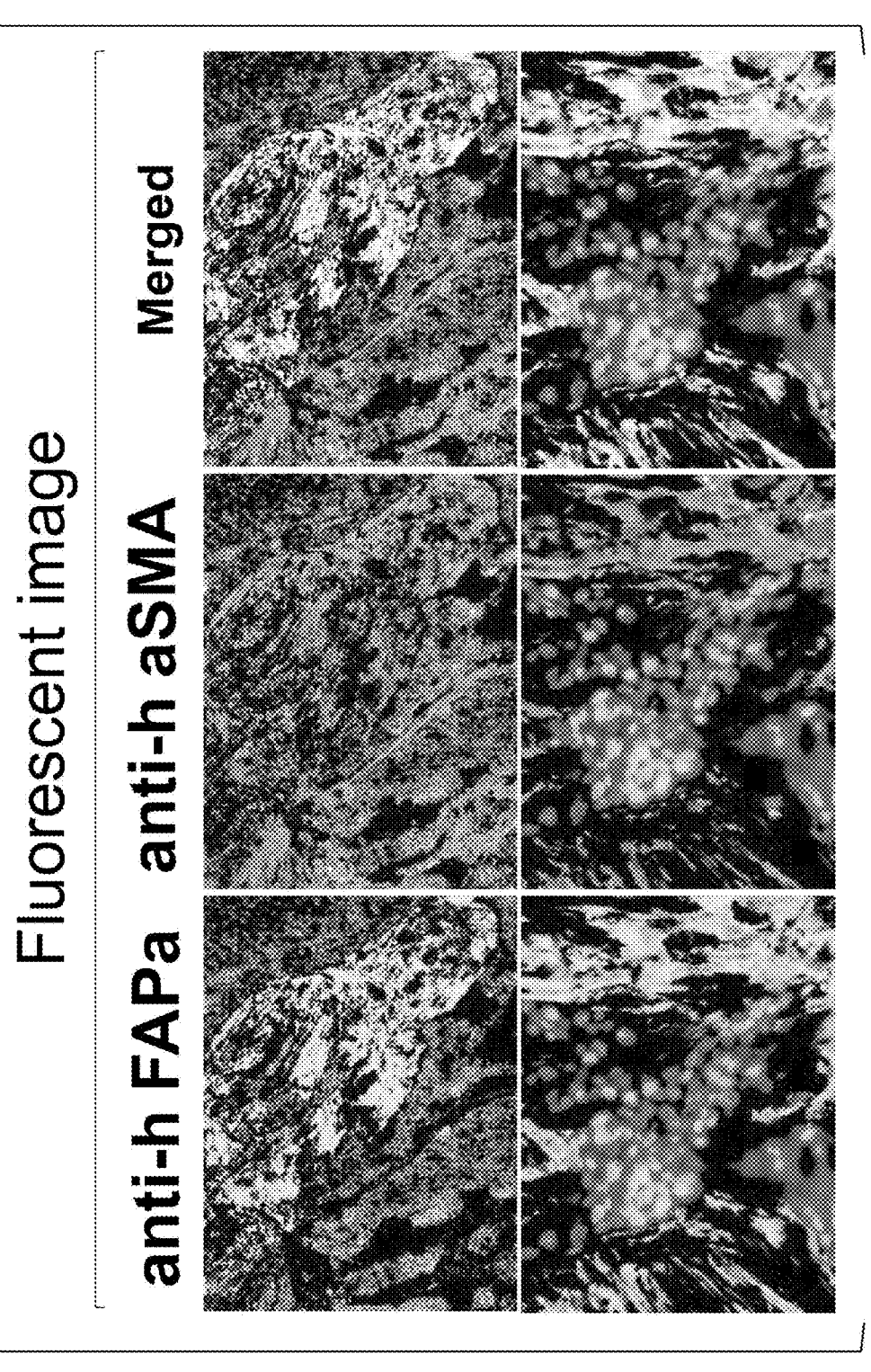
FIG. 8B is a series of fluorescent immunostaining images using anti-human FAPα antibody and anti-human αSMA antibody of a subcutaneous tumor in a mouse in Example 8.

FIG. 8B is a series of fluorescent immunostaining images using anti-human fibroblast activation protein-α (FAPα) antibody and anti-human smooth muscle actin-α (SMAα) antibody of the subcutaneous tumor. In FIG. 8B, "Merge" represents a merged image of the fluorescent immunostaining image using anti-FAPα antibody and the fluorescent immunostaining image using anti-SMAα antibody. FAPα and SMAα are known as CAF positive markers. The high-density accumulated mass of the nucleus that exists in the central portion of each of the enlarged photographs shown in the lower row in the figure are cancer cell nest portions formed by the cancer cells themselves, whereas the cancer stroma is the proliferation of fibroblasts that develop around the periphery of these cancer cell nests.

Figure 8C:
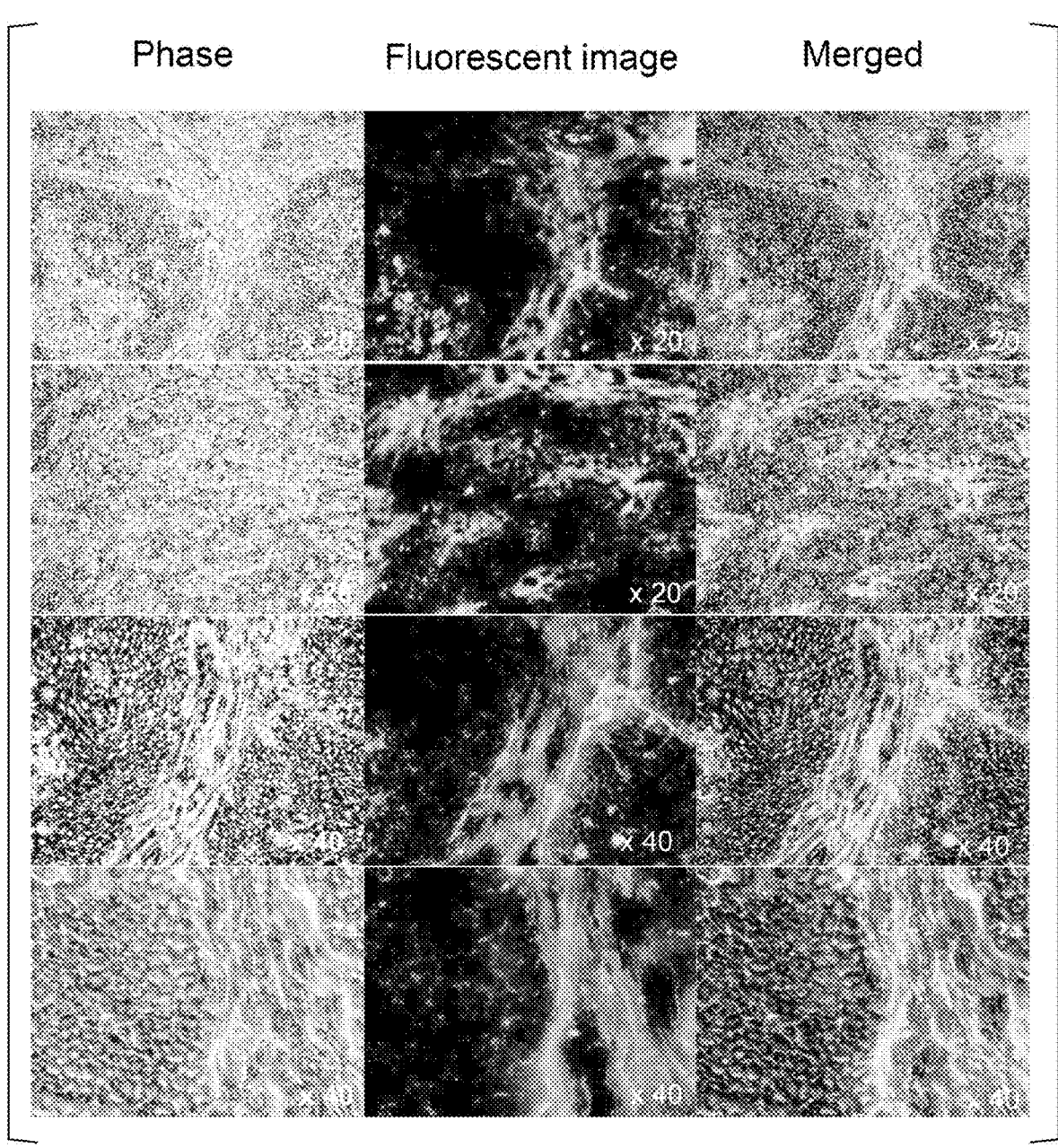
FIG. 8C is a series of phase difference microscope images and fluorescent images of a subcutaneous tumor in a mouse in Example 8.

FIG. 8C is a series of phase difference microscope images and fluorescent images of the subcutaneous tumor. The upper two rows are images at a magnification of 20×, whereas the lower two rows are images at a magnification of 40×. Further, "Merge" represents merged images of each phase difference microscope image and each fluorescent image.

Based on FIG. 8A, the subcutaneous tumor was histologically determined to be a scirrhous cancer (hard cancer) containing abundant cancer stroma.

Based on FIG. 8B, it was confirmed that the cells that existed in the cancer stroma were CAF.

Based on FIG. 8C, it was ascertained that the fluorescence derived from the administered peptide was observed only in the fibrous stroma portions that develop between cancer cell nests, confirming that tandem MSCPP106 exhibits selective absorption into the CAF of the cancer stroma.

Example 9

(Absorption of [FAM]-Tandem MSCPP106 and [FAM]-Tandem Mut MSCPP106 into Cancer Stroma in In-Vivo System)

Next, in order to investigate the functional importance of the cysteine within the peptide sequence (positioned second from the N-terminus), a comparison was made of the absorption into cancer stroma of [FAM]-tandem MSCPP106 and [FAM]-tandem mut MSCPP106 (having a sequence in which the N-terminus is labeled with FAM, and having a mutation in which the side-chain —SH group of the cysteine second from the N-terminus has been methylated). With the exception of using cloned hMSC cells that constantly expressed DsRed2, the same method as Example 7 was used to obtain scirrhous pancreatic cancer model mice. Subsequently, the obtained scirrhous pancreatic cancer model mice were injected intravenously with [FAM]-tandem MSCPP106 or [FAM]-tandem mut MSCPP106 (300 µg in each case). In each case, the pharmacokinetics of the peptide 60 minutes after the intravenous injection were then analyzed by tissue analysis of the freshly dissected specimen of the peptide-administered mouse. The results are shown in FIG. 9A to FIG. 9E.

Figure 9A:
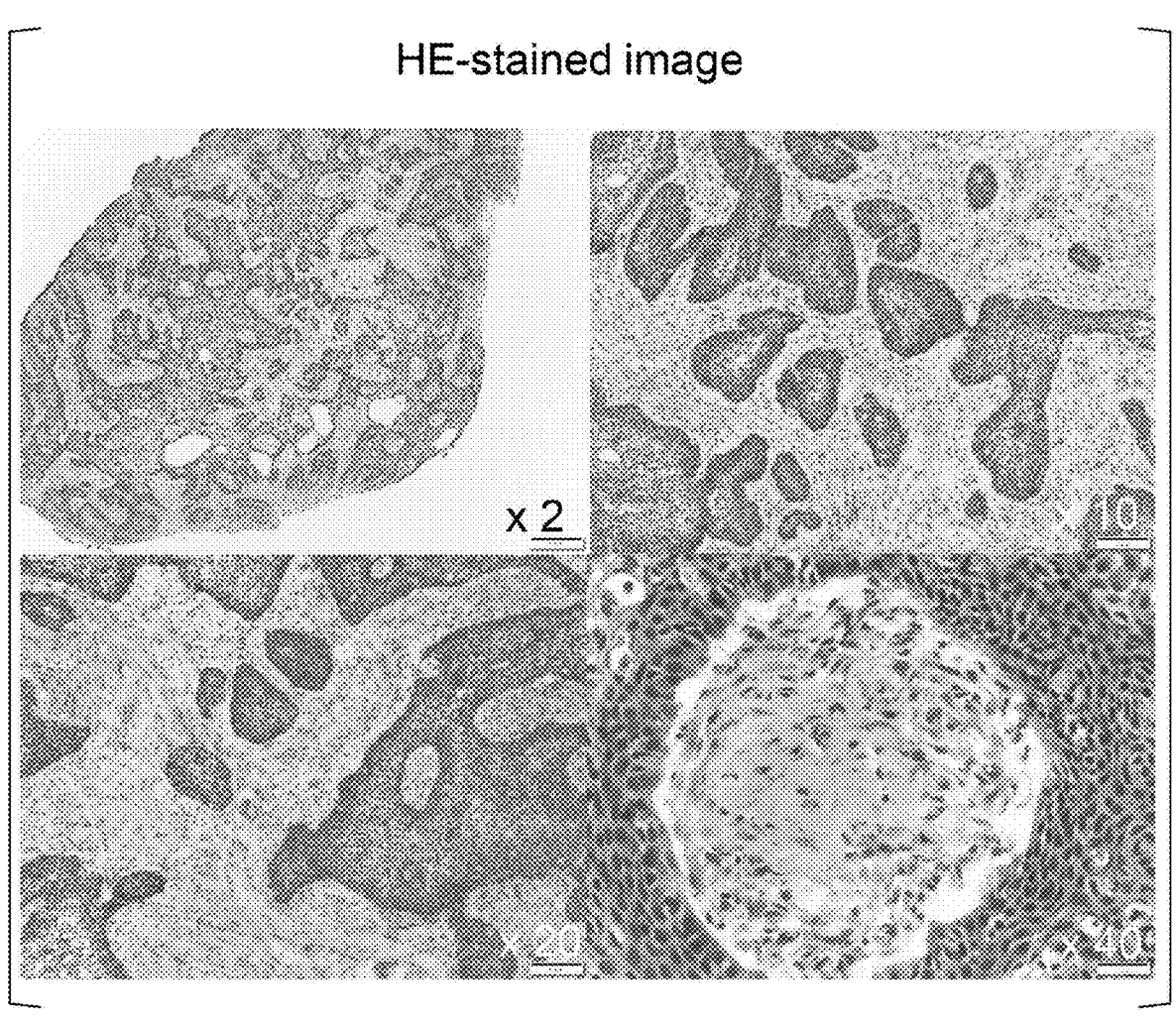
FIG. 9A is a series of HE-stained images of a subcutaneous tumor in a mouse in Example 9.

FIG. 9A is a series of HE-stained images of a subcutaneous transplanted tumor as an administration model (magnification: 2×, 10×, 20× and 40×).

Figure 9B:
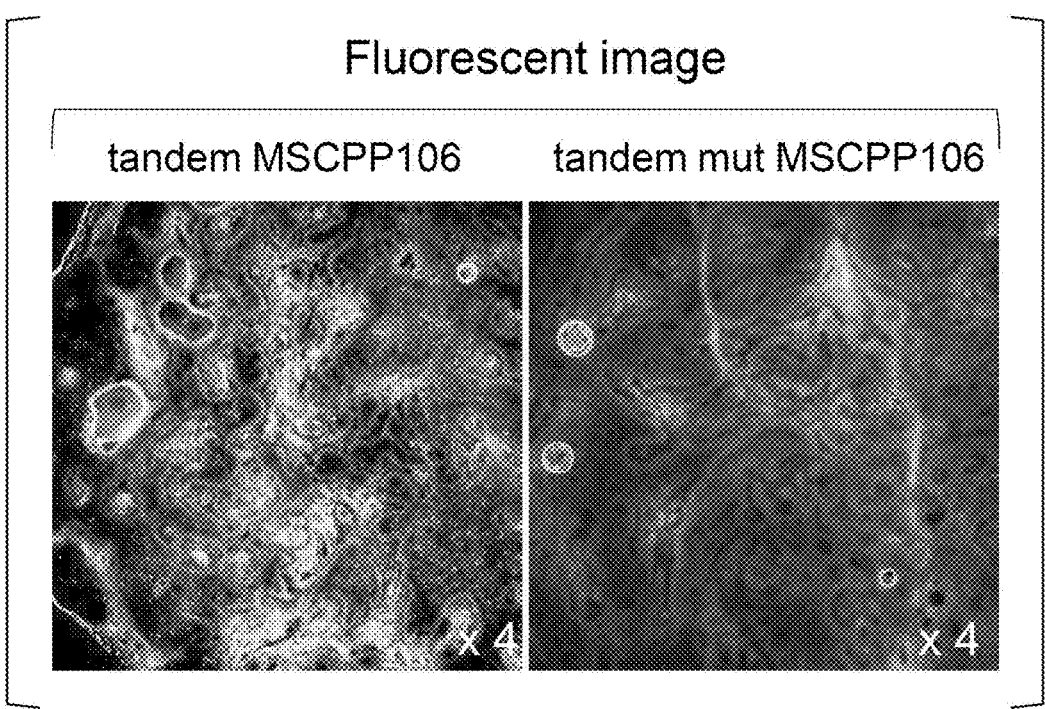
FIG. 9B is a series of fluorescent images of subcutaneous tumors in mice to which various peptides have been administered in Example 9.

FIG. 9B is a series of fluorescent images of subcutaneous tumors in mice administered with [FAM]-tandem MSCPP106 or [FAM]-tandem mut MSCPP106 (magnification: 4×).

Figure 9C:
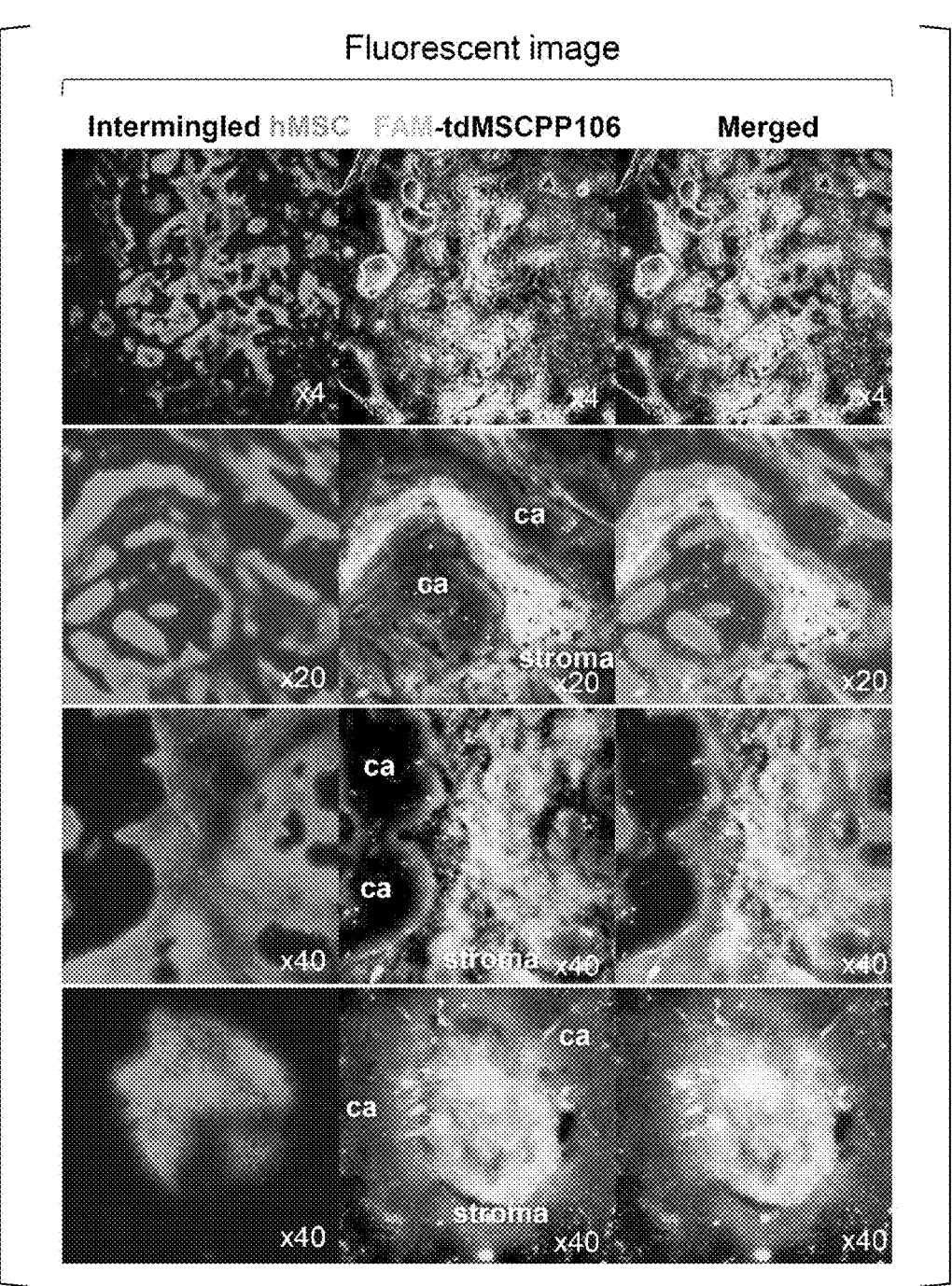
FIG. 9C is a series of fluorescent images of a subcutaneous tumor in a mouse to which [FAM]-tandem MSCPP106 has been administered in Example 9.

FIG. 9C is a series of fluorescent images of a subcutaneous transplanted tumor in a mouse administered with tandem MSCPP106 (magnification: 4×, 20× and 40×). In FIG. 9C, the left-hand column represents fluorescent images of fluorescence (DsRed2) derived from hMSC that have been intermingled and transplanted with pancreatic cancer cells BxPC3, the middle column represents fluorescent images of fluorescence (FAM) derived from the intravenously administered peptide (tdMSCPP106), and the right-hand column represents (merged) images obtained by merging the DsRed2 fluorescent images and the FAM fluorescent images. In FIG. 9C, "ca" is an abbreviation of "cancer", and indicates pancreatic cancer cell nest portions. The CAF develop and proliferate from the peripheral portions of hMSC accumulated in the cancer stroma.

Figure 9D:
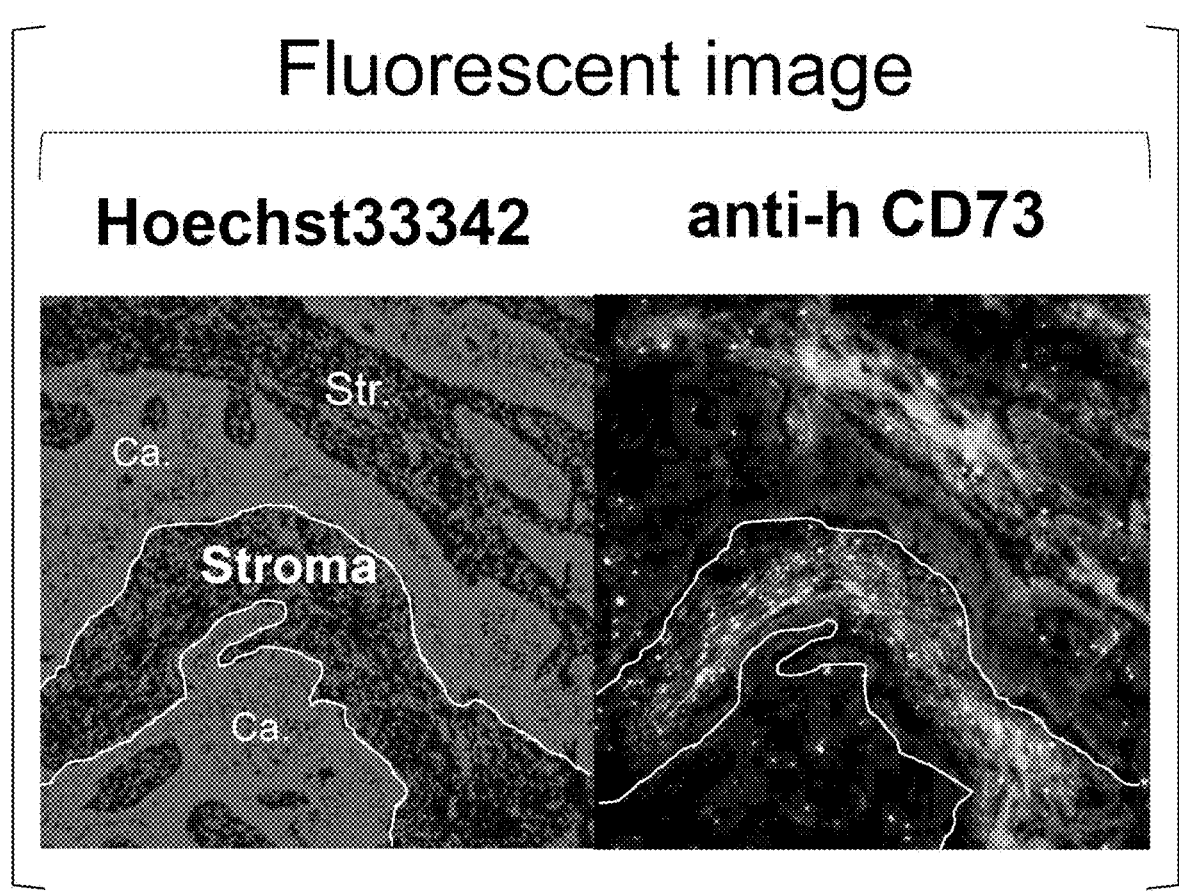
FIG. 9D is a series of fluorescent immunostaining images using anti-human CD73 antibody of a subcutaneous tumor in a mouse in Example 9.

FIG. 9D is a series of fluorescent immunostaining images using anti-human CD73 antibody of the subcutaneous tumor. Currently, in the field of cancer medical research, the development of anti-human CD73 antibody drugs for targeting cancer stroma is progressing worldwide. In FIG. 9D, "ca" is an abbreviation of "cancer", and indicates cancer cell nest portions. Further, "Str." is an abbreviation of "stroma", and indicates the cancer stroma. CD73 is a positive marker for hMSC and hCAF (and is expressed by a partial grouping of MSC and CAF), and is widely used as a cell marker for detecting CAF that exists in the stroma of cancer tissue.

Figure 9E:
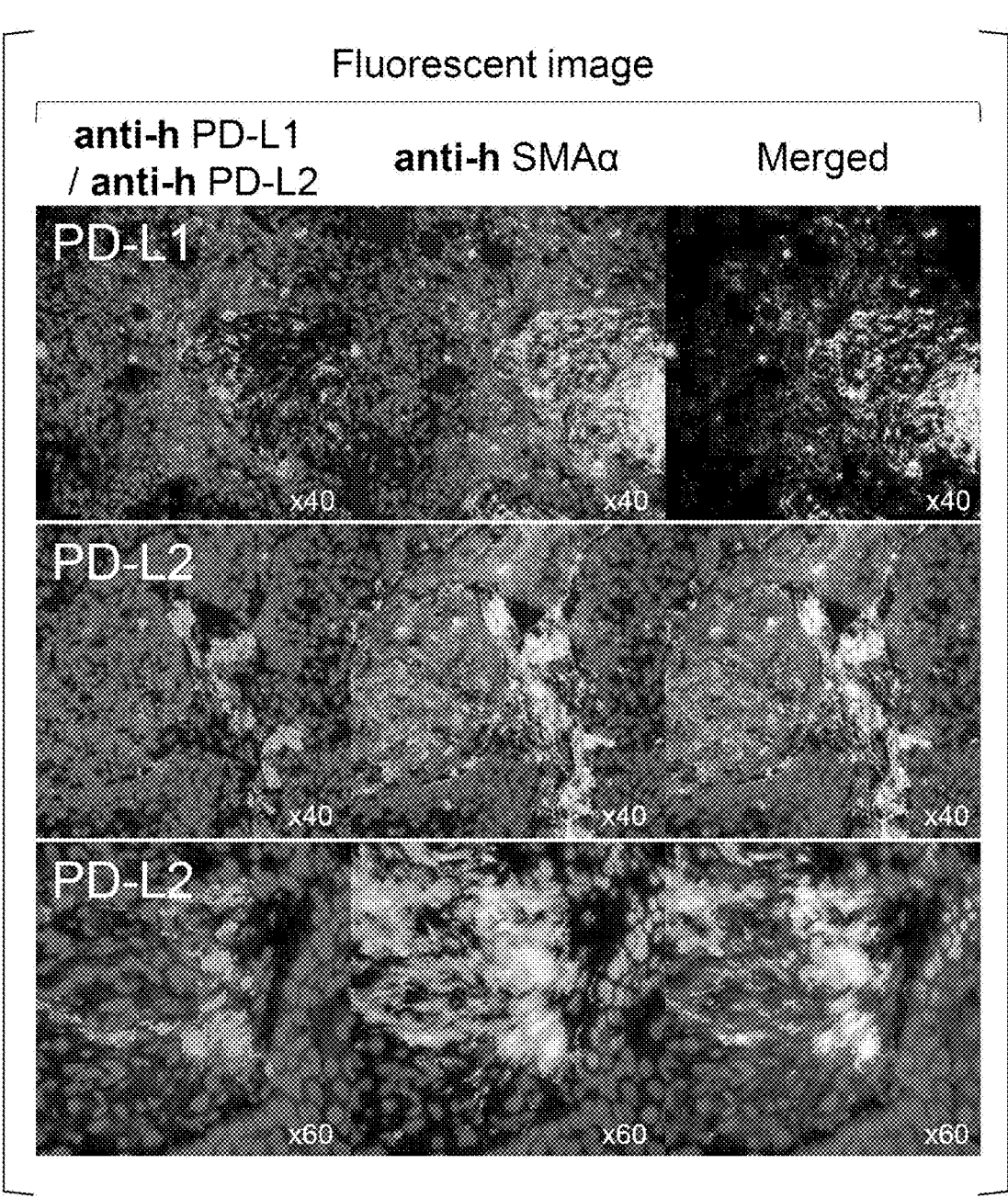
FIG. 9E is a series of fluorescent immunostaining images using anti-PD-L1 antibody, anti-PD-L2 antibody and anti-SMAα antibody of a subcutaneous tumor in a mouse in Example 9.

FIG. 9E is a series of fluorescent immunostaining images using the anti-human PD-L1 antibody, anti-human PD-L2 antibody and anti-human SMAα antibody of a mouse transplanted model subcutaneous tumor (magnification: 40× and 60×). In FIG. 9E, "Merge" indicates merged images of the corresponding left-hand image (the fluorescent immunostaining image using the anti-human PD-L1 antibody or anti-human PD-L2 antibody) and the middle image (the fluorescent immunostaining image using the anti-human SMAα antibody).

Based on FIG. 9A, it was confirmed that the mouse subcutaneous tumor exhibited a morphology rich in stroma cells with cells derived from the BxPC3 cells existing in the form of islands.

Based on FIG. 9B, it was ascertained that tandem MSCPP106 had even better absorption into cancer stroma than tandem mut MSCPP106. Based on this result, it is thought that the SH group side chain of the cysteine contributes to the cyclization or polymerization of the peptide, thereby significantly improving the absorption efficiency of the peptide into the cancer stroma, thus indicating the importance of the cysteine residue in the peptide sequence.

Based on FIG. 9C, it was ascertained that the cancer stroma contained both human cell-derived CAF (hCAF) obtained by induced differentiation from the administered hMSC, and CAF obtained by induced differentiation from MSC within the body of the mouse, with the tandem MSCPP106 exhibiting excellent absorption into both forms of CAF. Further, based on the anti-human CD73 specific antibody stained images shown in FIG. 9D, it was ascertained that the cancer stroma in the mouse transplanted tumor model included a structural component having intermingles hCAF differentially induced from hMSC. As a result of comparing FIG. 9C and FIG. 9D, it is predicted that tandem MSCPP106 exhibits stroma absorption that greatly exceeds the reactive range of the anti-CD73 antibody, and that when used to target cancer stroma, has a comprehensive targeting performance that is superior to that of the anti-CD73 antibody.

Based on FIG. 9E, it was ascertained that in the subcutaneous pancreatic cancer model tumor in the mouse that had been administered with BxPC3 cells and hMSC, PD-L1 and PD-L2 were expressed significantly in a portion of the CAF, in a similar manner to that observed in the cancer stroma of pancreatic cancer tissue in human invasive pancreatic ductal adenocarcinoma patients. In other words, it was determined that not only the pancreatic cancer cells themselves, but also the pancreatic cancer stroma is a type of immune-resistant tissue that uses a mechanism which avoids attack by the main lymphocytic immune cells as a biological defense mechanism. As described above, histologically, pancreatic cancer tissue is composed of invasive cell nests formed from cancer cells and a thickly developed stroma that surrounds those cell nests, but if this multiply resistant stroma can be eliminated, then the tumor can be weakened or destroyed. Accordingly, the structure of the means used for targeting the cancer stroma is extremely important in destruction of the cancer. Consequently, by administering a composition in which an anticancer drug is bound to a peptide such as tandem MSCPP106 that exhibits absorption into the cancer stroma, the development of anti-cancer treatments that function by extensively destroying CAF can be expected. Moreover, by using such compositions together with immune checkpoint inhibitors such as Nivolumab or Pembrolizumab, a more powerful cancer stroma destruction effect, or a synergistic antitumor effect that simultaneously attacks both the cancer cells and the cancer stroma can be expected.

Example 10

(Absorption of [FAM]-Tandem MSCPP106 into Cancer Stroma of Scirrhous Stomach Cancer in In-Vivo System)

Stomach poorly differentiated scirrhous adenocarcinoma, which is an example of a typical scirrhous carcinoma, is classified by visual classification into type 4 stomach cancer, and this type 4 stomach cancer has an extremely poor prognosis, with a five-year survival rate of about at least 4% but not more than 16%. Accordingly, in order to investigate the application of [FAM]-tandem MSCPP106 to the CAF that develop in the scirrhous stroma of cancer other than pancreatic cancer, a scirrhous stomach cancer mouse transplanted model was produced, and the absorption into scirrhous cancer stroma other than pancreatic cancer was investigated. With the exceptions of using human stomach poorly differentiated adenocarcinoma HSC58 cells instead of the BxPC3 cells, and rearing the mouse for 40 days from the time of cell injection, the same method as Example 7 was used to obtain a scirrhous stomach cancer mouse model. The HSC58 cells are a low metastatic human scirrhous stomach cancer cell line. Subsequently, [FAM]-tandem MSCPP106 (300 μg) was injected intravenously into the obtained scirrhous cancer mouse model, and the in-vivo absorption pharmacokinetics of the peptide 60 minutes after the intravenous injection were analyzed by tissue analysis of the freshly dissected specimen of the peptide-administered mouse. The results are shown in FIG. 10A and FIG. 10B.

Figure 10A:
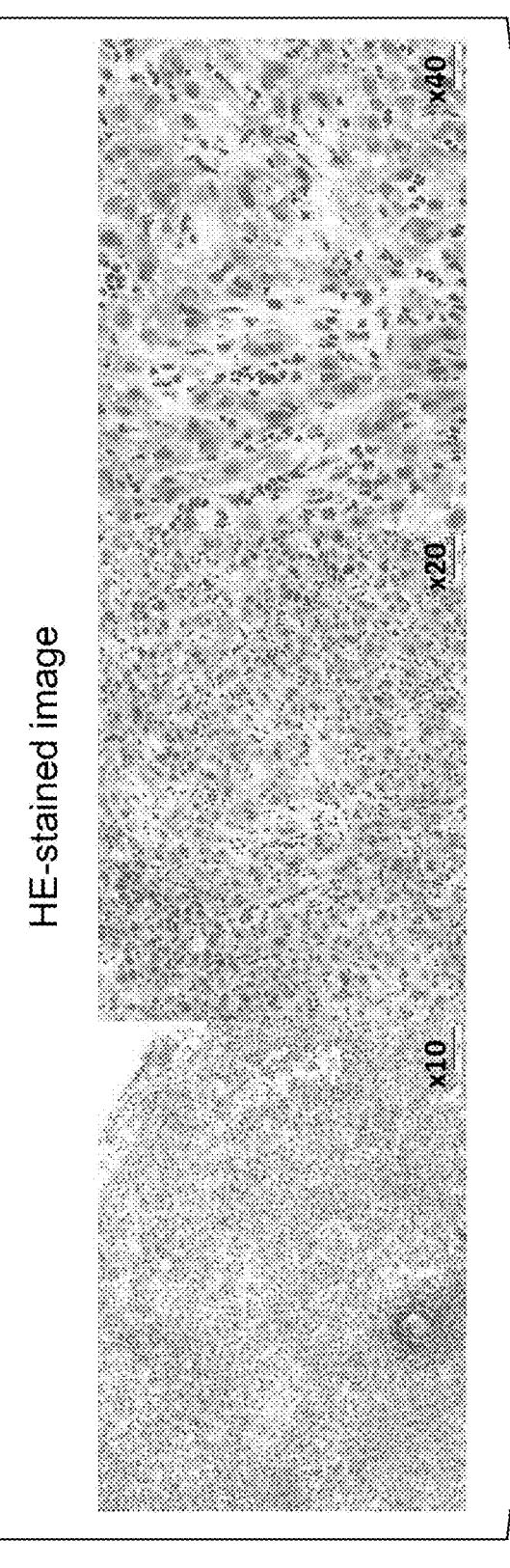
FIG. 10A is a series of HE-stained images of an abdominal tumor in Example 10.

FIG. 10A is a series of HE-stained images of an abdominal tumor (magnification: 10×, 20× and 40×).

Figure 10B:
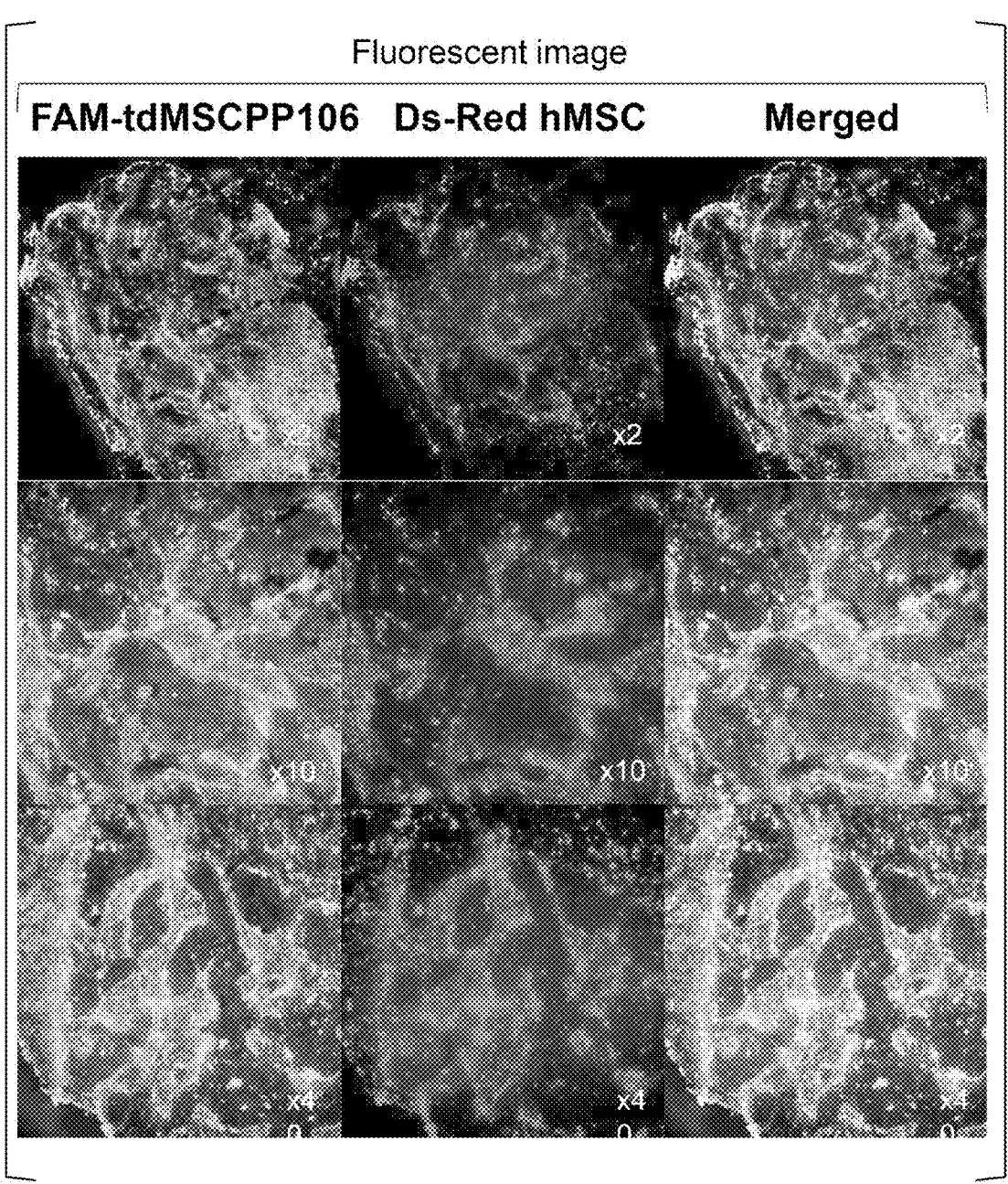
FIG. 10B is a series of fluorescent images of an abdominal tumor in Example 10.

FIG. 10B is a series of fluorescent images of the abdominal tumor (magnification: 2×, 10× and 40×). The images in the left-hand column are FAM fluorescent images derived from the administered peptide, the images in the middle column are DsRed2 fluorescent images derived from the mixed and transplanted hMSC, and the images in the right-hand column are merged images obtained by merging the corresponding FAM fluorescent image and DsRed2 fluorescent image.

Based on FIG. 10A, it was ascertained that the abdominal cavity transplanted tumor was a scirrhous carcinoma (hard cancer) containing abundant stroma between the cancer cell nests, thus imitating the tissue in human scirrhous stomach cancer.

Based on FIG. 10B, it was confirmed that [FAM]-tandem MSCPP106 also exhibited strong selective absorption into the cancer stroma of the stomach scirrhous carcinoma, in a similar manner to that observed for the cancer stroma of pancreatic cancer.

INDUSTRIAL APPLICABILITY

A peptide of an embodiment of the present invention can provide a novel peptide that accumulates in CAF. A carrier of an embodiment of the present invention contains this peptide, and can simply and efficiently transport a target substance into a cancer stroma that contains CAF or MSC.

The invention claimed is:

1. A peptide composed of an amino acid sequence represented by general formula (I) shown below:

$$X^{11} - \left(Y^{11} - X^{12}\right)_{n11} \qquad (I)$$

wherein in general formula (I), $X^{11}$ is a peptide residue composed of an amino acid sequence of (a), (b), or (c) below:

(a) an amino acid sequence represented by any one of SEQ ID NOs: 1 to 4, (b) an amino acid sequence in which the first lysine from the N-terminus of SEQ ID NO: 1 is substituted with glycine, alanine, arginine, histidine, serine, or threonine;

(c) an amino acid sequence in which one or two amino acids are deleted, substituted, or added in an amino acid sequence represented by any one of SEQ ID NOs: 2 to 4;

$Y^{11}$ is a peptide linker composed of an amino acid residue of at least 1 but not more than 10 amino acids, wherein each amino acid residue is independently a glycine residue, a proline residue, a serine residue, a cysteine residue, or a lysine residue;

$X^{12}$ is either a peptide residue composed of an amino acid sequence of (a) or (b) above, or a retro-inverso peptide residue thereof; and n11 is an integer of at least 1 but not more than 4.

2. The peptide according to claim 1, wherein $Y^{11}$ is a peptide linker composed of a glycine residue of at least 1 but not more than 10 amino acids.

3. The peptide according to claim 1, wherein $X^{11}$ and $X^{12}$ are peptide residues composed of the same amino acid sequence.

4. The peptide according to claim 1, composed of an amino acid sequence represented by SEQ ID NO: 5.

5. A peptide-drug-conjugate comprising a peptide of claim 1 and a biologically active substance.

6. A pharmaceutical composition comprising a peptide-drug-conjugate of claim 5.

7. The pharmaceutical composition according to claim 6, wherein the biologically active substance is an anticancer drug.

8. A labeled peptide comprising a peptide of claim 1 and a labeling substance.

9. The labeled peptide according to claim 8, wherein the labeling substance is biotin, avidin, streptavidin, a stable isotope, a radioisotope, or a fluorescent substance.

10. An imaging composition comprising a labeled peptide of claim 8.

11. The peptide according to claim 2, wherein Y11 is a peptide linker composed of an amino acid residue of at least 1 but not more than 5 amino acids.

12. A nucleic acid that encodes a peptide of claim 1.

13. A peptide-drug-conjugate expression vector comprising a nucleic acid of claim 12 and a nucleic acid that encodes a biologically active substance.

14. A labeled peptide expression vector comprising a nucleic acid of claim 12 and a nucleic acid that encodes a labeling substance.

* * * * *

SEQUENCE LISTING

<160> NUMBER OF SEQ ID NOS: 14

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Lys Cys Ala Glu Leu Phe Arg His Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Trp Pro Pro Leu Gln Arg Trp Arg Asn
1               5

<210> SEQ ID NO 3
<211> LENGTH: 9
<212> TYPE: PRT
<213> ORGANISM: Artificial Sequence
<220> FEATURE:
<223> OTHER INFORMATION: Synthesized

<400> SEQUENCE: 3

Arg Thr His Pro Val Trp Ser Arg Thr
1               5

<210> SEQ ID NO 4
<211> LENGTH: 9
<212> TYPE: PRT
<213> ORGANISM: Artificial Sequence
<220> FEATURE:
<223> OTHER INFORMATION: Synthesized

<400> SEQUENCE: 4

Arg Arg Trp Met Gln Trp Pro Trp His
1               5

<210> SEQ ID NO 5
<211> LENGTH: 19
<212> TYPE: PRT
<213> ORGANISM: Artificial Sequence
<220> FEATURE:
<223> OTHER INFORMATION: Synthesized

<400> SEQUENCE: 5

Lys Cys Ala Glu Leu Phe Arg His Leu Gly Lys Cys Ala Glu Leu Phe
1               5                   10                  15

Arg His Leu

<210> SEQ ID NO 6
<211> LENGTH: 19
<212> TYPE: PRT
<213> ORGANISM: Artificial Sequence
<220> FEATURE:
<223> OTHER INFORMATION: Synthesized
<220> FEATURE:
<221> NAME/KEY: MISC_FEATURE
<222> LOCATION: (2)..(2)

<223> OTHER INFORMATION: Xaa indicates Methyl-Cys.
<220> FEATURE:
<221> NAME/KEY: MISC_FEATURE
<222> LOCATION: (12)..(12)
<223> OTHER INFORMATION: Xaa indicates Methyl-Cys.

<400> SEQUENCE: 6

Lys Xaa Ala Glu Leu Phe Arg His Leu Gly Lys Xaa Ala Glu Leu Phe
1               5                   10                  15

Arg His Leu

<210> SEQ ID NO 7
<211> LENGTH: 27
<212> TYPE: DNA
<213> ORGANISM: Artificial Sequence
<220> FEATURE:
<223> OTHER INFORMATION: Synthesized

<400> SEQUENCE: 7
aagtgcgccg agctgttccg gcacctg                                       27

<210> SEQ ID NO 8
<211> LENGTH: 27
<212> TYPE: DNA
<213> ORGANISM: Artificial Sequence
<220> FEATURE:
<223> OTHER INFORMATION: Synthesized

<400> SEQUENCE: 8 tggcccccc tgcagcggtg gcggaac                                        27

<210> SEQ ID NO 9
<211> LENGTH: 27
<212> TYPE: DNA
<213> ORGANISM: Artificial Sequence
<220> FEATURE:
<223> OTHER INFORMATION: Synthesized

<400> SEQUENCE: 9
cggacccacc ccgtgtggtc ccggacc                                       27

<210> SEQ ID NO 10
<211> LENGTH: 27
<212> TYPE: DNA
<213> ORGANISM: Artificial Sequence
<220> FEATURE:
<223> OTHER INFORMATION: Synthesized

<400> SEQUENCE: 10
cggcggtgga tgcagtggcc ctggcac                                       27

<210> SEQ ID NO 11
<211> LENGTH: 57
<212> TYPE: DNA
<213> ORGANISM: Artificial Sequence
<220> FEATURE:
<223> OTHER INFORMATION: Synthesized

<400> SEQUENCE: 11
aagtgcgccg agctgttccg gcacctgggc aagtgcgccg agctgttccg gcacctg      57

<210> SEQ ID NO 12
<211> LENGTH: 9
<212> TYPE: PRT
<213> ORGANISM: Artificial Sequence
<220> FEATURE:

-continued

```
<223> OTHER INFORMATION: Synthesized

<400> SEQUENCE: 12

Arg Arg Arg Arg Arg Arg Arg Arg Arg
1               5

<210> SEQ ID NO 13
<211> LENGTH: 9
<212> TYPE: PRT
<213> ORGANISM: Artificial Sequence
<220> FEATURE:
<223> OTHER INFORMATION: Synthesized

<400> SEQUENCE: 13

Arg Ala Arg Val Ala Trp Asp Trp Ile
1               5

<210> SEQ ID NO 14
<211> LENGTH: 9
<212> TYPE: PRT
<213> ORGANISM: Artificial Sequence
<220> FEATURE:
<223> OTHER INFORMATION: Synthesized

<400> SEQUENCE: 14

Trp Thr Arg Thr Gln Trp Pro Leu His
1               5
```